United States Patent
Pulé et al.

(10) Patent No.: US 10,919,951 B2
(45) Date of Patent: *Feb. 16, 2021

(54) CHIMERIC ANTIGEN RECEPTOR

(71) Applicant: AUTOLUS LIMITED, London (GB)

(72) Inventors: Martin Pulé, London (GB); Kwee Yong, London (GB); Lydia Lee, London (GB); Ben Draper, London (GB)

(73) Assignee: AUTOLUS LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/162,747

(22) Filed: Oct. 17, 2018

(65) Prior Publication Data

US 2019/0100571 A1    Apr. 4, 2019

Related U.S. Application Data

(63) Continuation of application No. 15/028,064, filed as application No. PCT/GB2014/053058 on Oct. 10, 2014, now Pat. No. 10,160,794.

(30) Foreign Application Priority Data

Oct. 10, 2013    (GB) .................................... 1317929

(51) Int. Cl.
| | |
|---|---|
| *C07K 14/725* | (2006.01) |
| *C07K 14/705* | (2006.01) |
| *A61K 35/17* | (2015.01) |
| *C07K 16/18* | (2006.01) |
| *C12N 15/85* | (2006.01) |
| *A61K 48/00* | (2006.01) |

(52) U.S. Cl.
CPC ........ *C07K 14/70578* (2013.01); *A61K 35/17* (2013.01); *C07K 14/7051* (2013.01); *C07K 14/70575* (2013.01); *C07K 16/18* (2013.01); *C12N 15/85* (2013.01); *A61K 48/00* (2013.01)

(58) Field of Classification Search
CPC ................................................. C07K 14/7051
See application file for complete search history.

(56) References Cited

U.S. PATENT DOCUMENTS

| | | | |
|---|---|---|---|
| 10,160,794 B2 * | 12/2018 | Pule ............... | A61K 35/17 |
| 2016/0362467 A1 | 12/2016 | Pule et al. | |
| 2017/0334964 A1 | 11/2017 | Pule et al. | |

FOREIGN PATENT DOCUMENTS

| | | |
|---|---|---|
| WO | WO-2002/18620 A2 | 3/2002 |
| WO | WO-2002/066516 A2 | 8/2002 |
| WO | WO-2008/003115 A1 | 1/2008 |
| WO | WO-2008/045437 A2 | 4/2008 |
| WO | WO-2013/072406 A1 | 5/2013 |
| WO | WO-2013/154760 A1 | 10/2013 |
| WO | WO-2018/087557 A1 | 5/2018 |
| WO | WO-2018/229492 A1 | 12/2018 |

OTHER PUBLICATIONS

Beitinjaneh et al., Durable responses after donor lymphocyte infusion for patients with residual multiple myeloma following non-myeloablative allogeneic stem cell transplant, *Leuk. Lymphoma.* 53:1525-9 (2012).

Carpenter et al., B-cell maturation antigen is a promising target for adoptive T-cell therapy of multiple myeloma. *Clin. Cancer Res.* 19:2048-60 (2013).

Guan et al., The construction and characterization of a bifunctional EGFP/sAPRIL fusion protein. *Appl. Microbiol. Biotechnol.* 73:1114-22 (2006).

Hombach et al., Adoptive immunotherapy with genetically engineered T cells: modification of the IgG1 Fc 'spacer' domain in the extracellular moiety of chimeric antigen receptors avoids 'off-target' activation and unintended initiation of an innate immune response. *Gene Ther.* 17:1206-13 (2010).

Ingold et al., Identification of proteoglycans as the APRIL-specific binding partners, *J. Exp. Med.* 201:1375-83 (2005).

Kalos et al., Adoptive T cell transfer for cancer immunotherapy in the era of synthetic biology. *Immunity.* 39: 49-60 (2013).

Kimberley et al., The design and characterization of receptor-selective APRIL variants, *J. Biol. Chem.* 287:37434-46 (2012).

Lee et al., Designing APRIL-based therapeutics for targeting BCMA in multiple myeloma. American Society of Gene and Cell Therapy 17th Annual Meeting: Simultaneous Oral Abstract Sessions in Cancer-Targeted Gene & Cell Therapy. http://www.abstracts2view.com/asgct/view.php?nu=ASGCT14L1_272, May 22, 2014.

Lee et al., Designing APRIL-based therapeutics for targeting BCMA in multiple myeloma. UK Myeloma Forum ASH 2013 Winning Abstracts (uploaded document created on Oct. 25, 2013, http://www.ukmf.org.uk/winners/ash-2013-new-orleans/, dated Jan. 5, 2015.

Maus et al., Zoom Zoom: Racing CARs for multiple myeloma. *Clin. Cancer Res.* 19:1917-9 (2013).

Pule et al., A chimeric T cell antigen receptor that augments cytokine release and supports clonal expansion of primary human T cells. *Molec. Ther.* 12:933-41 (2005).

Sadelain et al., The Basic Principles of Chimeric Antigen Receptor Design. *Cancer Discovery,* 3:388-98 (2013).

Yu et al., APRIL and TALL-I and receptors BCMA and TACI: System for regulating humoral immunity. *Nat. Immunol.* 1: 252-6 (2000).

(Continued)

*Primary Examiner* — Thaian N. Ton
*Assistant Examiner* — David A. Montanari
(74) *Attorney, Agent, or Firm* — Marshall, Gerstein & Borun LLP

(57) ABSTRACT

The present invention provides a chimeric antigen receptor (CAR) comprising; (i) a B cell maturation antigen (BCMA)-binding domain which comprises at least part of a proliferation-inducing ligand (APRIL); (ii) a spacer domain (iii) a transmembrane domain; and (iv) an intracellular T cell signaling domain. The invention also provides the use of such a T-cell expressing such a CAR in the treatment of plasma-cell mediated diseases, such as multiple myeloma.

7 Claims, 16 Drawing Sheets

Specification includes a Sequence Listing.

(56) References Cited

OTHER PUBLICATIONS

International Search Report and Written Opinion from corresponding International Application No. PCT/GB2014/053058 dated Feb. 4, 2015.
Lu et al,. "Advances in Research on Proliferation of Tumour Cells by APRIL," Chinese Journal of Cancer Biotherapy 12(3) (2005).

\* cited by examiner

FIG. 5A

METDTLLLWVLLLWVPGSTGSVLHLVPINATSKDDSDVTEVMWQPALRRGRGLQAQGYGVRIQDAGVYLLYSQ
VLFQDVTFTMGQVVSREGQGRQETLFRCIRSMPSHPDRAYNSCYSAGVFHLHQGDILSVIIPRARAKLNLSPH
GTFLGFVKL*SGGGSDP*TTTPAPRPPTPAPTIASQPLSLRPEACRPAAGGAVHTRGLDFACDIFWVLVVVGGVL
ACYSLLVTVAFIIFWVRSKRSRLLHSDYMNMTPRRPGPTRKHYQPYAPPRDFAAYRSRDQRLPPDAHKPPGGG
SFRTPIQEEQADAHSTLAKIRVKFSRSADAPAYQQGQNQLYNELNLGRREEYDVLDKRRGRDPEMGGKPRRKN
PQEGLYNELQKDKMAEAYSEIGMKGERRGKGHDGLYQGLSTATKDTYDALHMQALPPR

Fig. 5B

METDTLLLWVLLLWVPGSTGSVLHLVPINATSKDDSDVTEVMWQPALRRGRGLQAQGYGVRIQDAGVYLLYSQ
VLFQDVTFTMGQVVSREGQGRQETLFRCIRSMPSHPDRAYNSCYSAGVFHLHQGDILSVIIPRARAKLNLSPH
GTFLGFVKL*SGGGSDP*AEPKSPDKTHTCPPCPKDPKFWVLVVVGGVLACYSLLVTVAFIIFWVRSKRSRLLHS
DYMNMTPRRPGPTRKHYQPYAPPRDFAAYRSRDQRLPPDAHKPPGGGSFRTPIQEEQADAHSTLAKIRVKFSR
SADAPAYQQGQNQLYNELNLGRREEYDVLDKRRGRDPEMGGKPRRKNPQEGLYNELQKDKMAEAYSEIGMKGE
RRRGKGHDGLYQGLSTATKDTYDALHMQALPPR

FIG. 5C

METDTLLLWVLLLWVPGSTGSVLHLVPINATSKDDSDVTEVMWQPALRRGRGLQAQGYGVRIQDAGVYLLYSQ
VLFQDVTFTMGQVVSREGQGRQETLFRCIRSMPSHPDRAYNSCYSAGVFHLHQGDILSVIIPRARAKLNLSPH
GTFLGFVKL*SGGGSDP*AEPKSPDKTHTCPPCPAPPVAGPSVFLFPPKPKDTLMIARTPEVTCVVVDVSHEDPE
VKFNWYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGKKDPKFWVLVVVGGVLACYSLLVTVAFIIFWVRSKRSRLLHSDYM
NMTPRRPGPTRKHYQPYAPPRDFAAYRSRDQRLPPDAHKPPGGGSFRTPIQEEQADAHSTLAKIRVKFSRSAD
APAYQQGQNQLYNELNLGRREEYDVLDKRRGRDPEMGGKPRRKNPQEGLYNELQKDKMAEAYSEIGMKGERRR
GKGHDGLYQGLSTATKDTYDALHMQALPPR

| | |
|---|---|
| Signal Peptide | Efficient signal peptide |
| dAPRIL | Truncated APRIL |
| Spacer | Either hinge-CH2CH3 of human IgG1, human CD8α stalk and human IgG1 hinge |
| TM and endodomain | Compound endodomain comprising of the CD28TM domain, CD28 endodomain and OX40 and CD3-Zeta endodomains |

FIG. 15A

MGTSLLCWMALCLLGADHADG*KRTRNRIEGTDSTSGGGGS*VLHLVPINATSKDDSDVTEVMWQPALRRGRGLQ
AQGYGVRIQDAGVYLLYSQVLFQDVTFTMGQVVSREGQGRQETLFRCIRSMPSHPDRAYNSCYSAGVFHLHQG
DILSVIIPRARAKLNLSPHGTFLGFVKL*SGGGSDP*AEPKSPDKTHTCPPCPAPPVAGPSVFLFPPKPKDTLMI
ARTPEVTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGKKDPKFWVLVVVGGVLACYSLLVTVA
FIIFWVRSKRSRLLHSDYMNMTPRRPGPTRKHYQPYAPPRDFAAYRSRDQRLPPDAHKPPGGGSFRTPIQEEQ
ADAHSTLAKIRVKFSRSADAPAYQQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR

FIG. 15B

MGTSLLCWMALCLLGADHADG*KRTRNRIEGTDSTSGGGGS*VLHLVPINATSKDDSDVTEVMWQPALRRGRGLQ
AQGYGVRIQDAGVYLLYSQVLFQDVTFTMGQVVSREGQGRQETLFRCIRSMPSHPDRAYNSCYSAGVFHLHQG
DILSVIIPRARAKLNLSPHGTFLGFVKL*SGGGSDP*TTTPAPRPPTPAPTIASQPLSLRPEACRPAAGGAVHTR
GLDFACDIFWVLVVVGGVLACYSLLVTVAFIIFWVRSKRSRLLHSDYMNMTPRRPGPTRKHYQPYAPPRDFAA
YRSRDQRLPPDAHKPPGGGSFRTPIQEEQADAHSTLAKIRVKFSRSADAPAYQQGQNQLYNELNLGRREEYDV
LDKRRGRDPEMGGKPRRKNPQEGLYNELQKDKMAEAYSEIGMKGERRRGKGHDGLYQGLSTATKDTYDALHMQ
ALPPR

FIG. 15C

MGTSLLCWMALCLLGADHADG*KRTRNRIEGTDSTSGGGGS*VLHLVPINATSKDDSDVTEVMWQPALRRGRGLQ
AQGYGVRIQDAGVYLLYSQVLFQDVTFTMGQVVSREGQGRQETLFRCIRSMPSHPDRAYNSCYSAGVFHLHQG
DILSVIIPRARAKLNLSPHGTFLGFVKL*SGGGSDP*AEPKSPDKTHTCPPCPKDPKFWVLVVVGGVLACYSLLV
TVAFIIFWVRSKRSRLLHSDYMNMTPRRPGPTRKHYQPYAPPRDFAAYRSRDQRLPPDAHKPPGGGSFRTPIQ
EEQADAHSTLAKIRVKFSRSADAPAYQQGQNQLYNELNLGRREEYDVLDKRRGRDPEMGGKPRRKNPQEGLYN
ELQKDKMAEAYSEIGMKGERRRGKGHDGLYQGLSTATKDTYDALHMQALPPR

| Legend | Description |
|---|---|
| Signal Peptide | Efficient signal peptide |
| tag and linker | Epitope tag and linker (will be removed for production version, here for Western blotting etc). |
| dAPRIL | Truncated APRIL |
| spacer | Either hinge-CH2CH3 of human IgG1, human CD8α stalk and human IgG1 hinge |
| TM and endodomain | Compound endodomain comprising of the CD28TM domain, CD28 endodomain and OX40 and CD3-Zeta endodomains |

CHIMERIC ANTIGEN RECEPTOR

FIELD OF THE INVENTION

The present invention relates to chimeric antigen receptor (CAR) which binds the B cell maturation antigen (BCMA). T cells expressing such a CAR are useful in the treatment of plasma cell diseases such as multiple myeloma.

BACKGROUND TO THE INVENTION

Multiple Myeloma

Multiple Myeloma (myeloma) is a bone-marrow malignancy of plasma cells. Collections of abnormal plasma cells accumulate in the bone marrow, where they interfere with the production of normal blood cells. Myeloma is the second most common hematological malignancy in the U.S. (after non-Hodgkin lymphoma), and constitutes 13% of haematologic malignancies and 1% of all cancers. The disease is burdensome in terms of suffering as well as medical expenditure since it causes pathological fractures, susceptibility to infection, renal and then bone-marrow failure before death.

Unlike many lymphomas, myeloma is currently incurable. Standard chemotherapy agents used in lymphoma are largely ineffective for myeloma. In addition, since CD20 expression is lost in plasma cells, Rituximab cannot be used against this disease. New agents such as Bortezamib and Lenolidomide are partially effective, but fail to lead to long-lasting remissions.

There is thus a need for alternative agents for the treatment of myeloma which have increased efficacy and improved long-term effects.

Chimeric Antigen Receptors (CARs)

Chimeric antigen receptors are proteins which, in their usual format, graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 3).

The most common form of these molecules use single-chain variable fragments (scFv) derived from monoclonal antibodies to recognize a target antigen. The scFv is fused via a spacer and a transmembrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers. Carpenter et al (2013, Clin Cancer Res 19(8) 2048-60) describe a CAR which incorporates a scFv against the B-cell maturation antigen (BCMA).

BCMA is a transmembrane protein that is preferentially expressed in mature lymphocytes, i.e. memory B cells, plasmablasts and bone marrow plasma cells. BCMA is also expressed on multiple myeloma cells.

Carpenter et al demonstrate that T cells transduced to express the anti-BCMA CAR are capable of specifically killing myeloma cells from a plasmacytoma of a myeloma patient.

Although CAR approaches using anti-BCMA antibodies show promise, a particular consideration when targeting this antigen is the particularly low density of BCMA on myeloma cells, in comparison for instance with CD19 on a lymphoma cell. Hence there is a need to increase the sensitivity of target cell recognition of an anti-BCMA CART cell.

B-cell-activating factor (BAFF, TNFSF13B) interacts with BAFF-Receptor (BAFF-R, TNFRSF13C), B-cell membrane antigen (BCMA, TNFRSF17) and transmembrane activator and calcium modulator and cyclophilin ligand interactor (TACI, TNFRSF13B) while A proliferation-inducing ligand (APRIL, TNFSF13) interacts with BCMA, TACI and proteoglycans. BAFF-R activation affects peripheral B-cell survival, while BCMA may affect plasma cell survival. APRIL interaction with proteoglycans involves acidic sulphated glycol-saminoglycan side-chain containing amino-terminus of APRIL.

Figure 2:
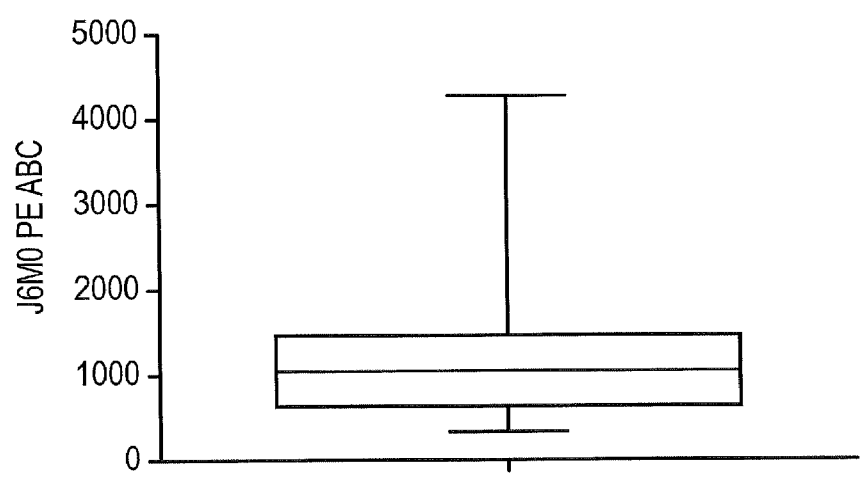

FIG. 2—Expression data of BCMA on Myeloma

Myeloma cells from bone marrow samples from 39 multiple myeloma patients were isolated by a CD138+ magnetic bead selection. These cells were stained with the anti-BCMA monoclonal antibody J6MO conjugated with PE (GSK). Antigen copy number was quantified using PE Quantibrite beads (Becton Dickenson) as per the manufacturer's instructions. A box and whiskers plot of antigen copy number is presented along with the range, interquartile and median values plotted. We found the range is 348.7-4268.4 BCMA copies per cell with a mean of 1181 and a median of 1084.9.

Figure 3:
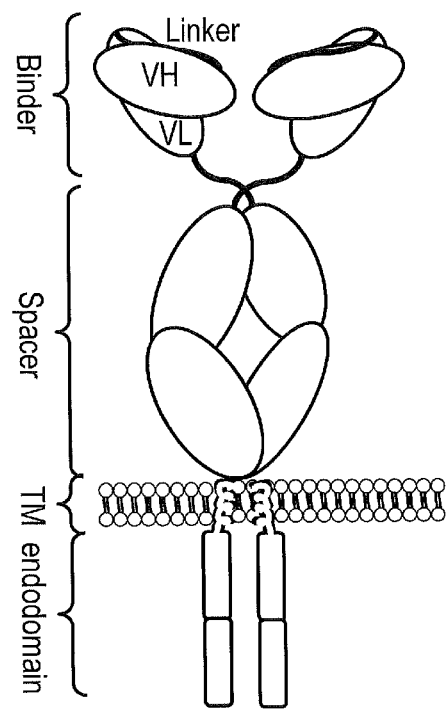

FIG. 3—Standard design of a Chimeric Antigen Receptor

The typical format of a chimeric antigen receptor is shown. These are type I transmembrane proteins. An ectodomain recognizes antigen. This is composed of an antibody derived single-chain variable fragment (scFv) which is attached to a spacer domain. This in turn is connected to a transmembrane domain which acts to anchor the molecule in the membrane. Finally, this is connected to an endodomain which acts to transmits intracellular signals to the cell. This is composed of one or more signalling domains.

FIG. 4—Design of the different APRIL-based CARs generated.

Figures 4A, 4B, 4C:
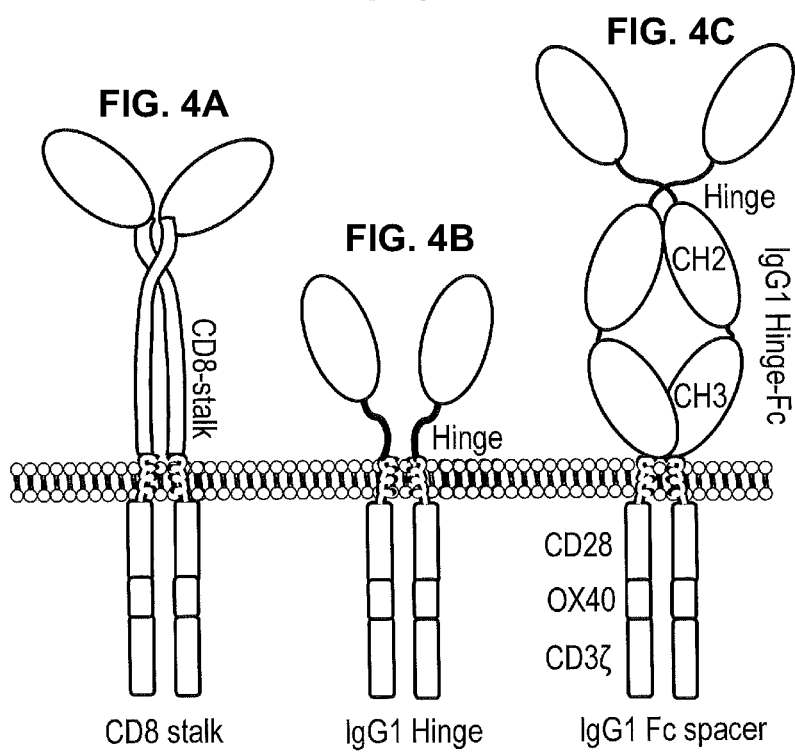

The CAR design as shown in FIG. 3 was modified so that the scFv was replaced with a modified form of APRIL to act as an antigen binding domain: APRIL was truncated so that the proteoglycan binding amino-terminus is absent. A signal peptide was then attached to truncated APRIL amino-terminus to direct the protein to the cell surface. Three CARs were generated with this APRIL based binding domain: FIG. 4A. In the first CAR, the human CD8 stalk domain was used as a spacer domain. FIG. 4B. In the second CAR, the hinge from IgG1 was used as a spacer domain. FIG. 4C. In the third CAR, the hinge, CH2 and CH3 domains of human IgG1 modified with the pva/a mutations described by Hombach et al (2010 Gene Ther. 17:1206-1213) to reduce Fc Receptor binding was used as a spacer (henceforth referred as Fc-pvaa). In all CARs, these spacers were connected to the CD28 transmembrane domain and then to a tripartite endodomain containing a fusion of the CD28, OX40 and the CD3-Zeta endodomain (Pule et al, Molecular therapy, 2005: Volume 12; Issue 5; Pages 933-41).

FIGS. 5A-5C Annotated Amino acid sequence of the above three APRIL-CARS FIG. 5A: Shows the annotated amino acid sequence of the CD8 stalk APRIL CAR; FIG. 5B: Shows the annotated amino acid sequence of the APRIL IgG1 hinge based CAR; FIG. 5C: Shows the annotated amino acid sequence of the APRIL Fc-pvaa based CAR.

Figure 6A:
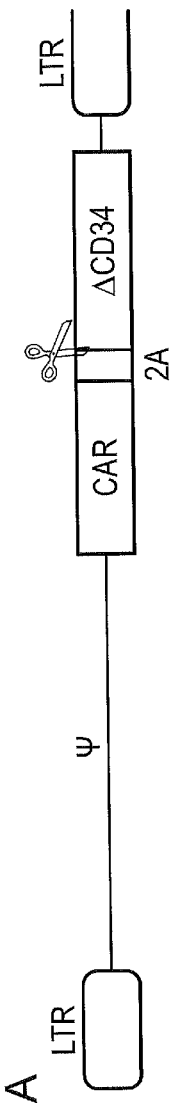
Figure 6B:
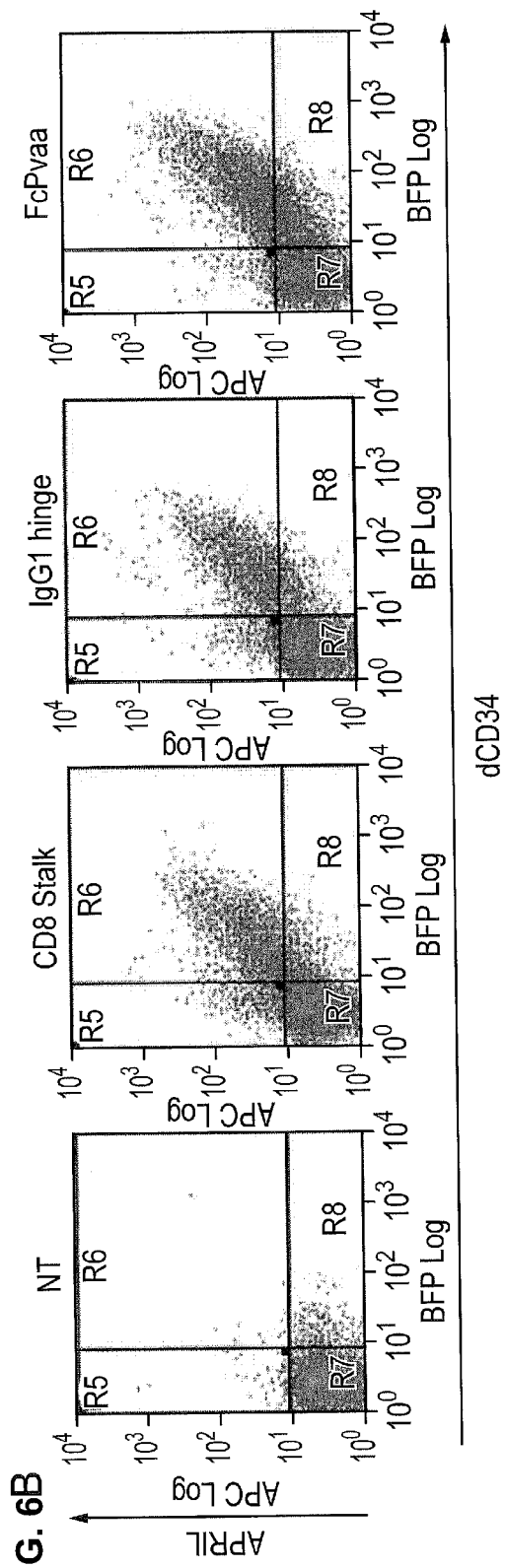
Figure 6C:
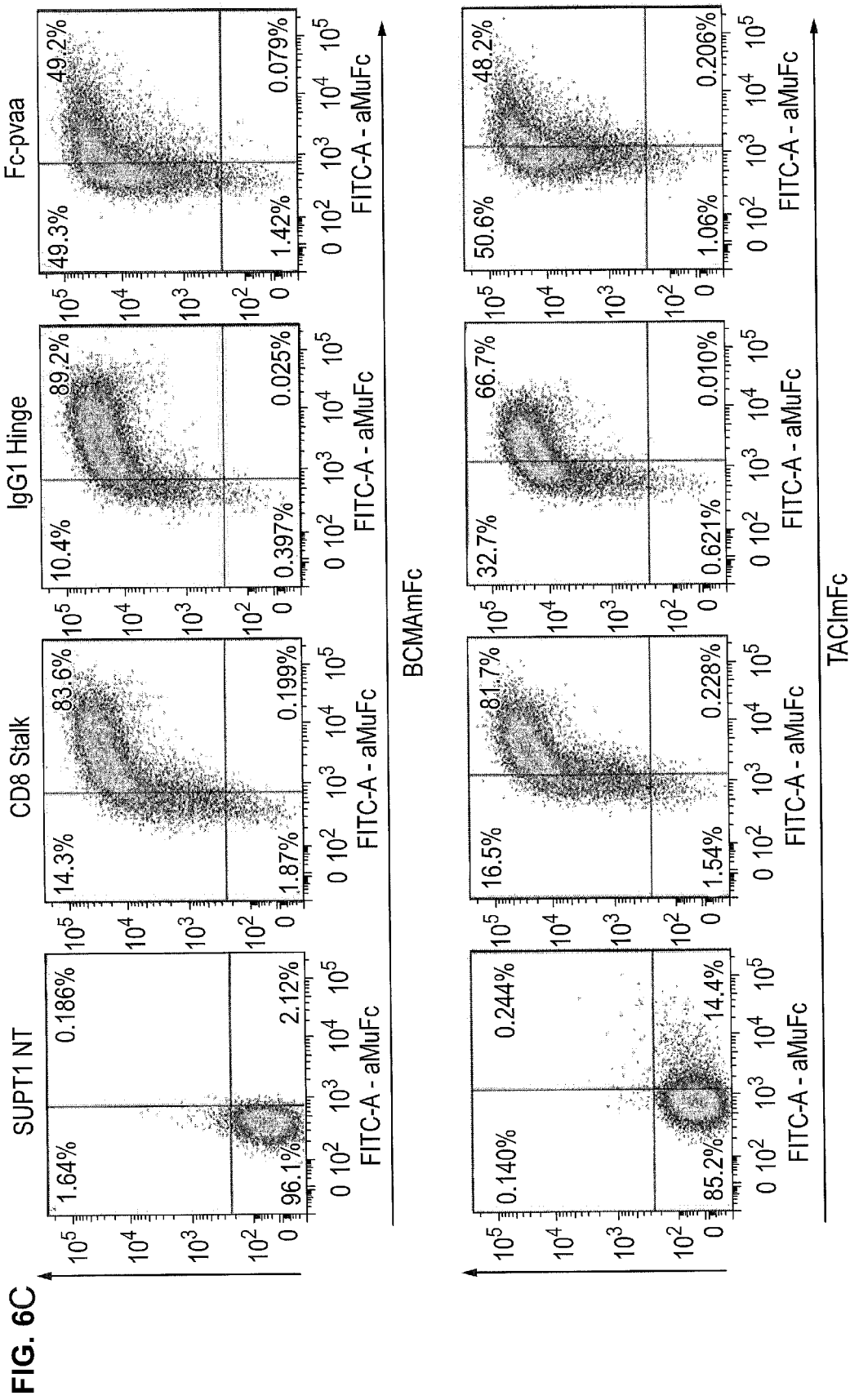

FIGS. 6A-6C—Expression and ligand binding of different APRIL based CARs

FIG. 6A. The receptors were co-expressed with a marker gene truncated CD34 in a retroviral gene vector. Expression of the marker gene on transduced cells allows confirmation of transduction. FIG. 6B. T-cells were transduced with APRIL based CARs with either the CD8 stalk spacer, IgG1 hinge or Fc spacer. To test whether these receptors could be stably expressed on the cell surface, T-cells were then stained with anti-APRIL-biotin/Streptavidin APC and anti-CD34. Flow-cytometric analysis was performed. APRIL was equally detected on the cell surface in the three CARs suggesting they are equally stably expressed. FIG. 6C. Next, the capacity of the CARs to recognize TACI and BCMA was determined. The transduced T-cells were stained with either recombinant BCMA or TACI fused to mouse IgG2a Fc fusion along with an anti-mouse secondary and anti-CD34. All three receptor formats showed binding to both BCMA and TACI. A surprising finding was that binding to BCMA seemed greater than to TACI. A further surprising finding was that although all three CARs were equally expressed, the CD8 stalk and IgG1 hinge CARs appeared better at recognizing BCMA and TACI than that with the Fc spacer.

Figure 7A:
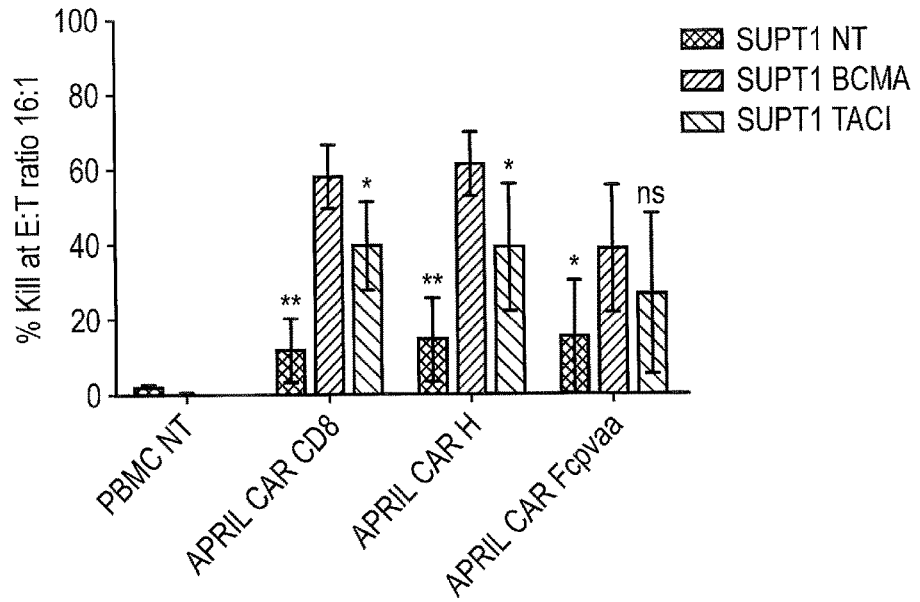
Figure 7B:
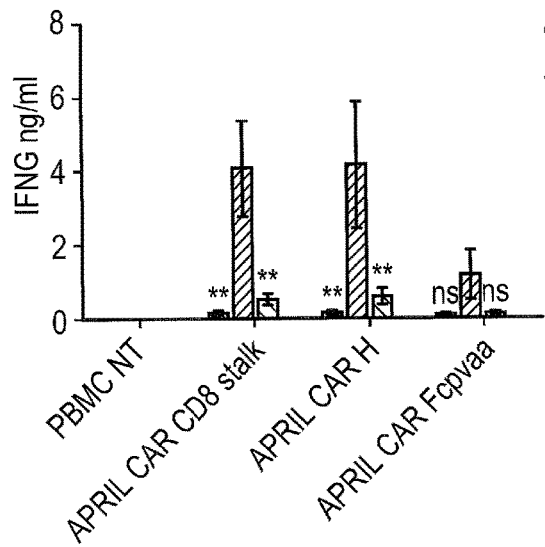
Figure 7C:
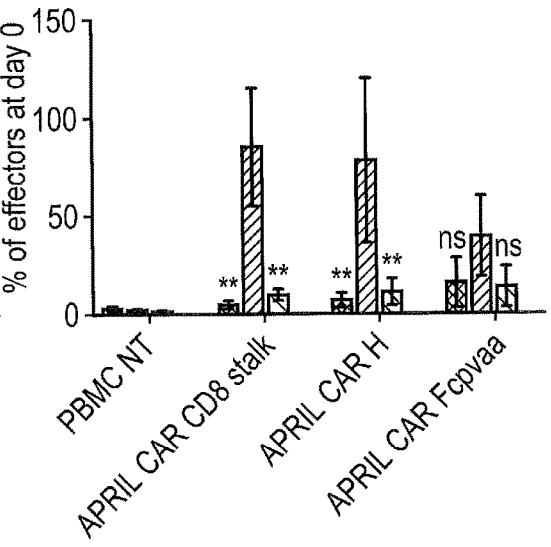

FIGS. 7A-7C—Function of the different CAR constructs.

Functional assays were performed of the three different APRIL based CARs. Normal donor peripheral blood T-cells either non-transduced (NT), or transduced to express the different CARs. Transduction was performed using equal titer supernatant. These T-cells were then CD56 depleted to remove non-specific NK activity and used as effectors. SupT1 cells either non-transduced (NT), or transduced to express BCMA or TACI were used as targets. Data shown is mean and standard deviation from 5 independent experiments. FIG. 7A. Specific killing of BCMA and TACI expressing T-cells was determined using Chromium release. FIG. 7B. Interferon-γ release was also determined. Targets and effectors were co-cultured at a ratio of 1:1. After 24 hours, Interferon-γ in the supernatant was assayed by ELISA. FIG. 7C. Proliferation/survival of CAR T-cells were also determined by counting number of CAR T-cells in the same co-culture incubated for a further 6 days. All 3 CARs direct responses against BCMA and TACI expressing targets. The responses to BCMA were greater than for TACI.

Figure 8:
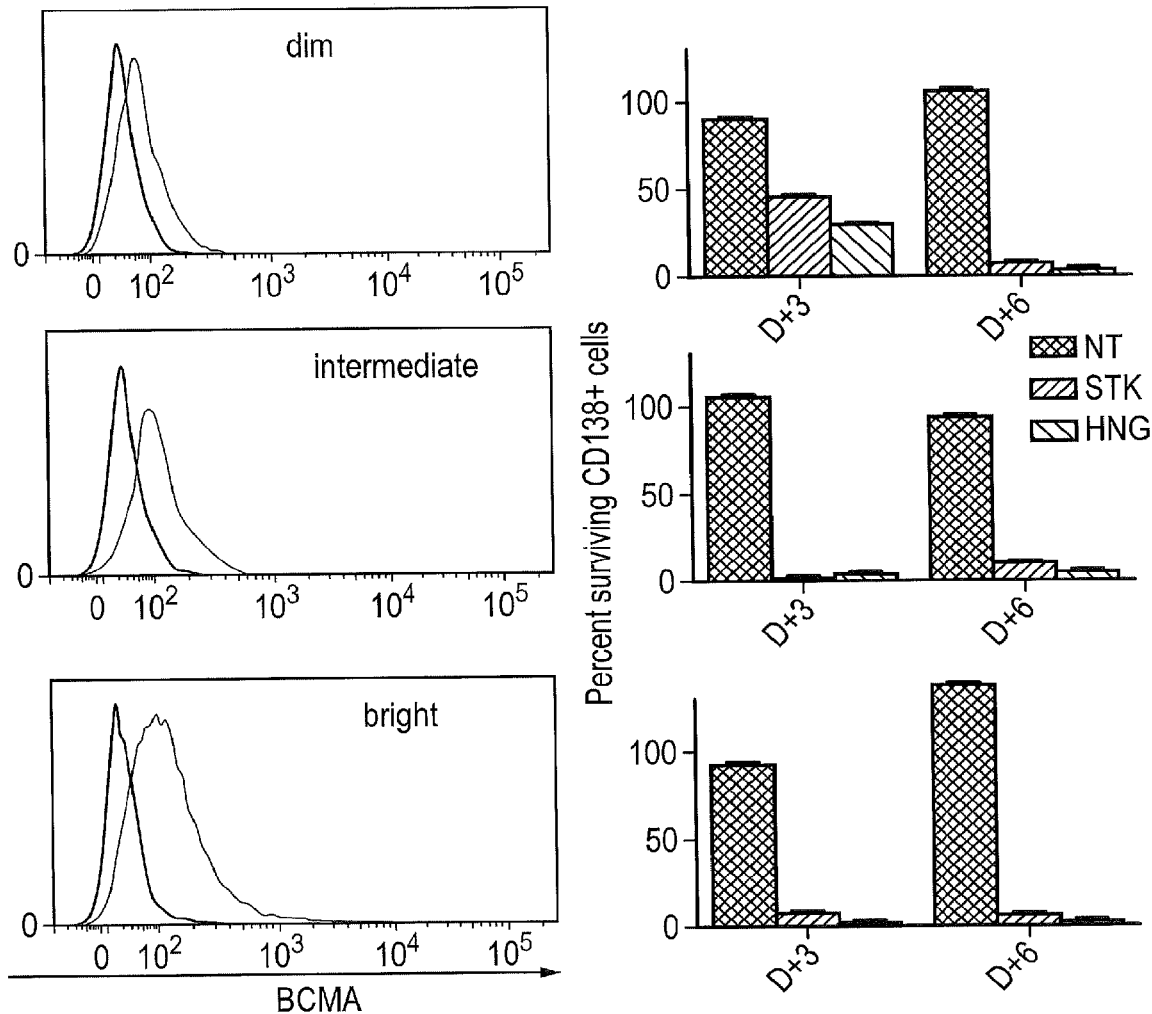

FIG. 8—Killing of primary Myeloma cells by APRIL CAR T-cells

Since most primary myeloma cells express a low number of BCMA molecules on their surface, it was investigated whether killing of primary myeloma cells occurs despite low-density expression. Three cases were selected which represented the range of BCMA expression described in FIG. 2: the first had dim expression (lower than mean); the second case had intermediate expression (approximately mean expression) and the third had bright (above mean expression). A histogram of BCMA staining against isotype control for all three cases is shown on the left. In this assay, only the CD8 stalk and hinge APRIL CARs were tested. On the left, survival of myeloma cells compared with starting numbers is shown at day 3 and day 6 after a 1:1 co-culture of myeloma cells and CAR T-cells. By day 6, >95% of the myeloma cells were eliminated, including those with dim BCMA expression.

Figure 9:
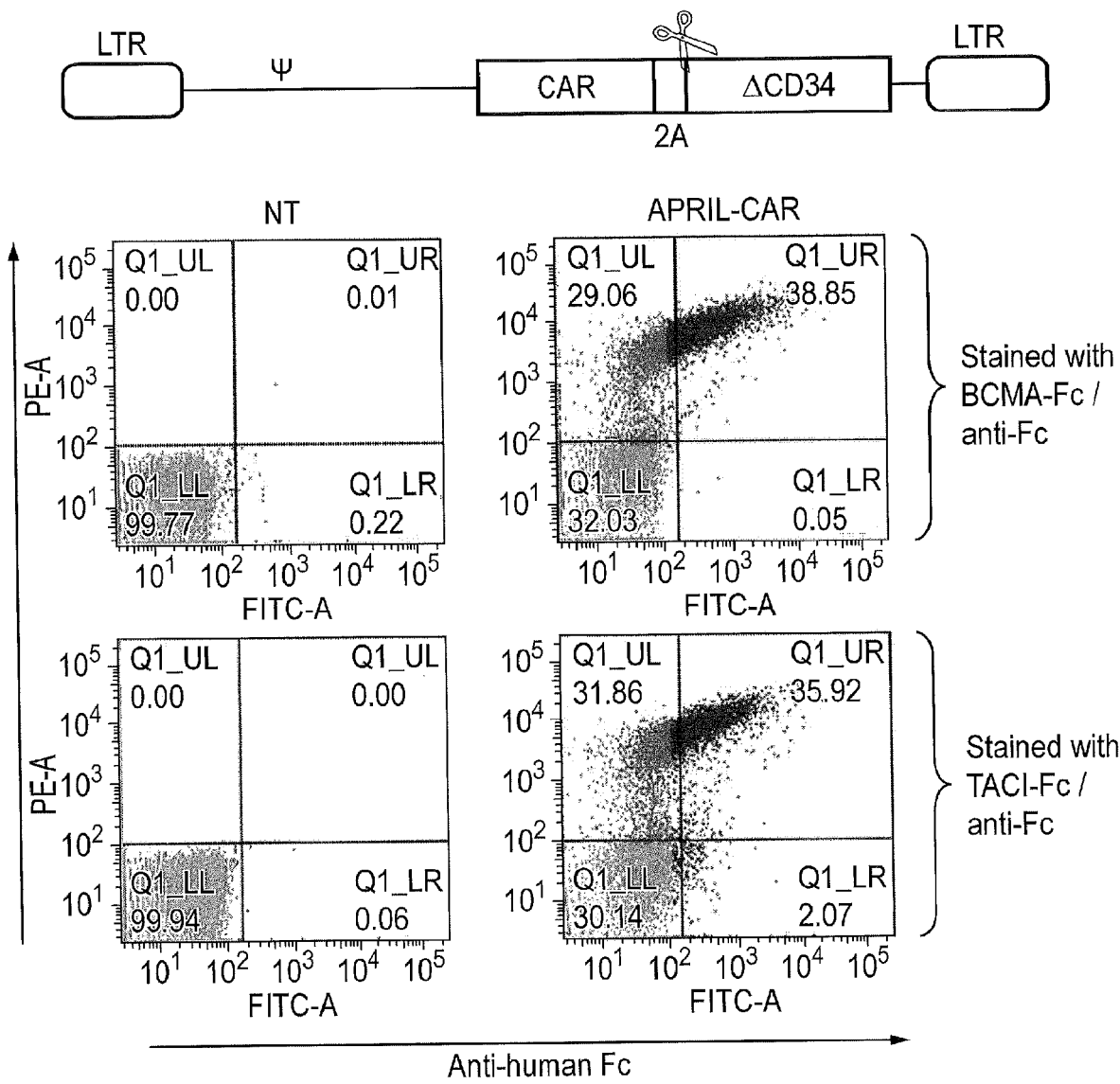

FIG. 9—Vector co-expressing APRIL based CAR with truncated CD34

A cell line expressing the vector used for screening was incubated with either BCMA-Fc or TACI-Fc and stained with both anti-CD34 and anti-human-Fc PE and FITC conjugated mAbs. The cells were then studied by flow-cytometry. This shows a typical pattern of binding of BCMA and TACI relative to the marker gene CD34.

Figure 10A:
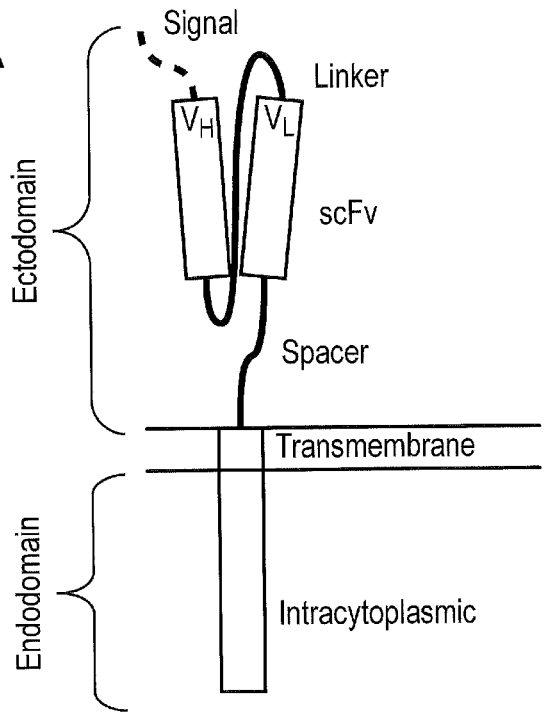
Figure 10B:
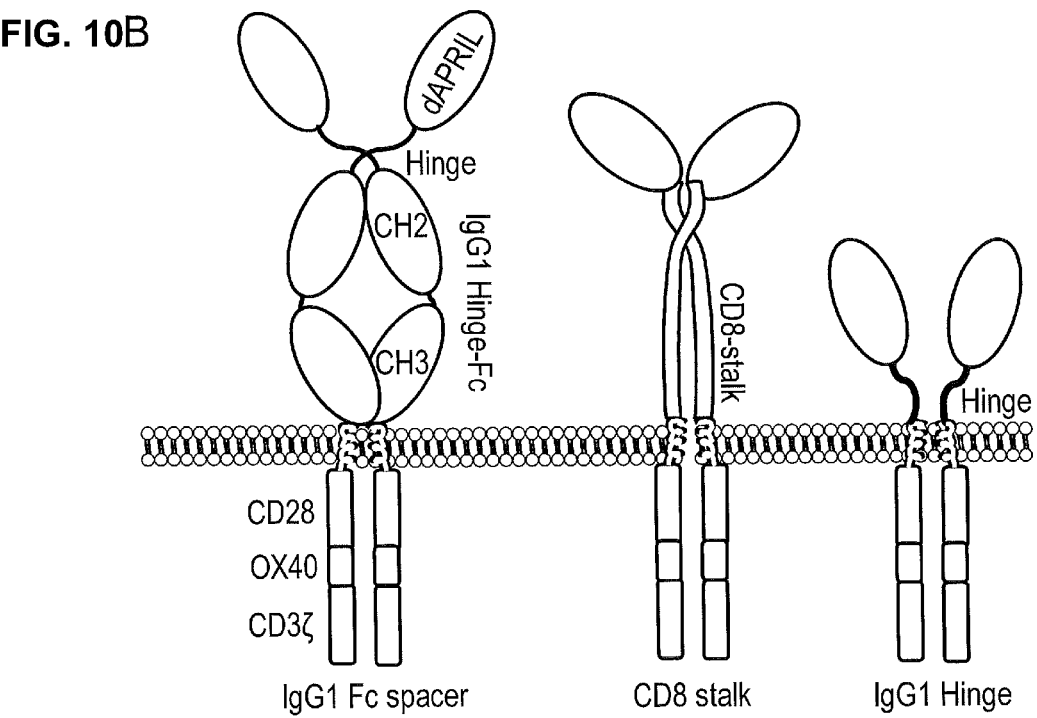

FIGS. 10A-10B—FIG. 10A Schematic diagram illustrating a classical CAR

FIG. 10B Design of the different APRIL-based CARs generated.

A signal peptide is attached to truncated APRIL amino-terminus. This was fused to different spacers: either the hinge, CH2 and CH3 domains of human IgG1 modified with the pvaa mutation described by Hombach et al (2010 Gene Ther. 17:1206-1213) to reduce Fc Receptor binding; the stalk of human CD8a; and the hinge of IgG1. These spacers were connected to a tripartite endodomain containing CD28 transmembrane domain, the OX40 endodomain and the CD3-Zeta endodomain.

Figure 11:
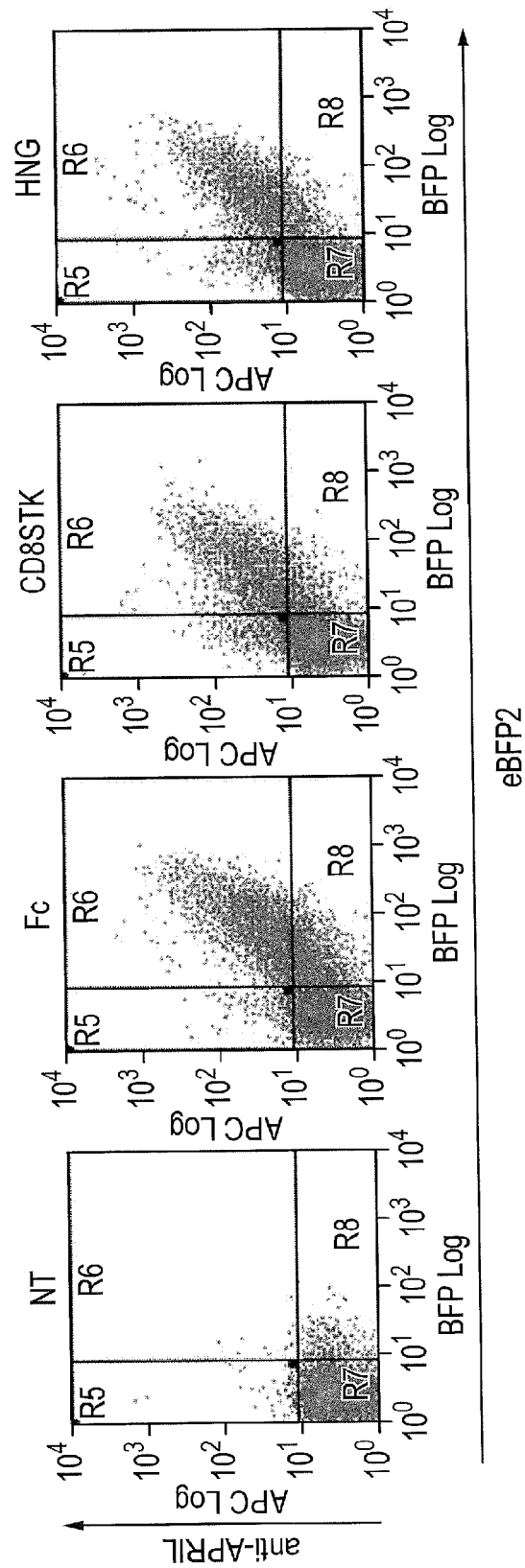

FIG. 11—Expression of different CARs

The receptors were co-expressed with enhanced blue fluorescence protein 2 (eBFP2) using an IRES sequence. Primary human T-cells were transduced and stained with anti-APRIL-biotin/Streptavidin APC. Flow-cytometric analysis was performed. eBFP2 signal is shown against APRIL detection. All three CARs are stably expressed (representative experiment of 3 independent experiments performed using 3 different normal donor T-cells).

Figure 12:
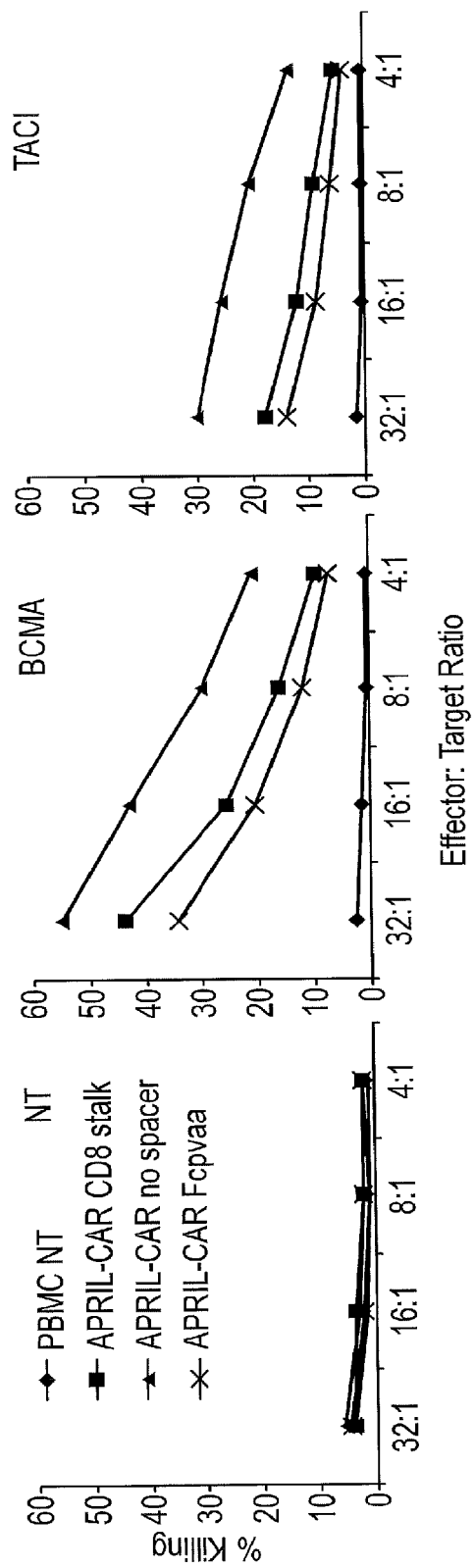

FIG. 12—Chromium release assay

Using normal donor peripheral blood T-cells either non-transduced (NT), or transduced to express different spacer CARs as effectors, and SupT1 cells either non-transduced (NT), or transduced to express BCMA or TACI as targets. The T-cells were CD56 depleted to reduce NK activity. This is a representative of three independent experiments and is shown as an example. Cumulative killing data is shown in FIG. 7A. Specific killing of BCMA and TACI expressing T-cells is seen with no activity against negative target cells.

Figure 13:
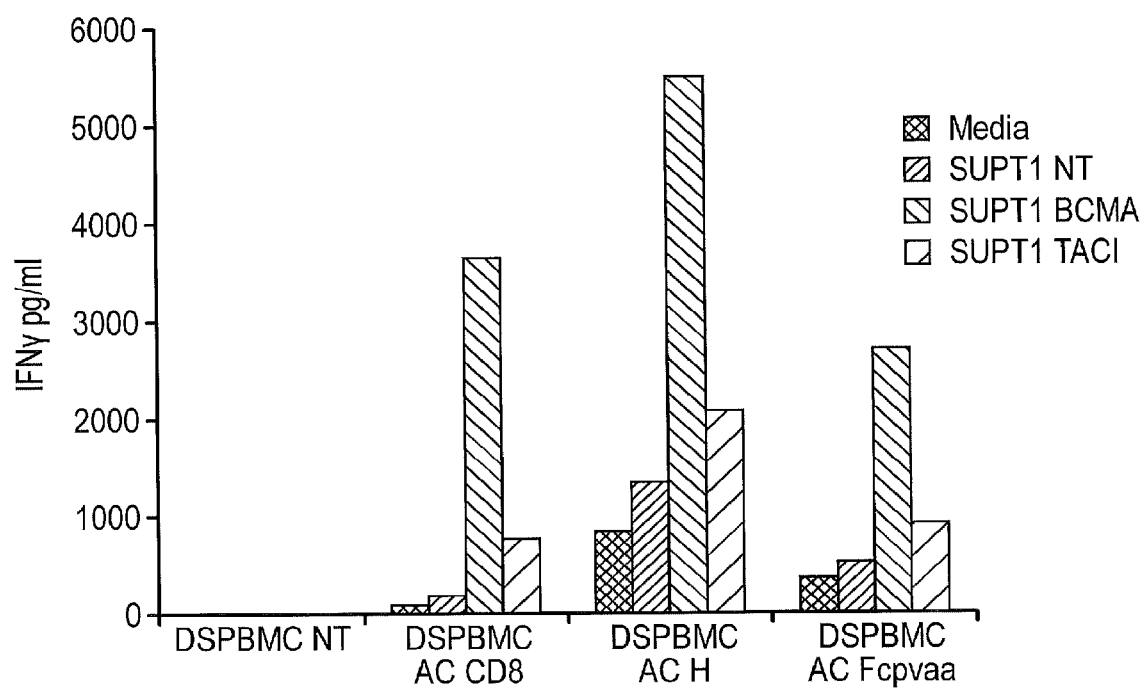

FIG. 13—Interferon-gamma release

From a 1:1 co-culture of effectors and targets is measured by ELISA. The CD8 stalk construct appears to have the best specificity while the hinge construct results in the most Interferon release demonstrates some non-specific activity. This is representative of 3 independent experiments and is shown as an example. Cumulative interferon-gamma release data is shown in FIG. 7B.

Figure 14:
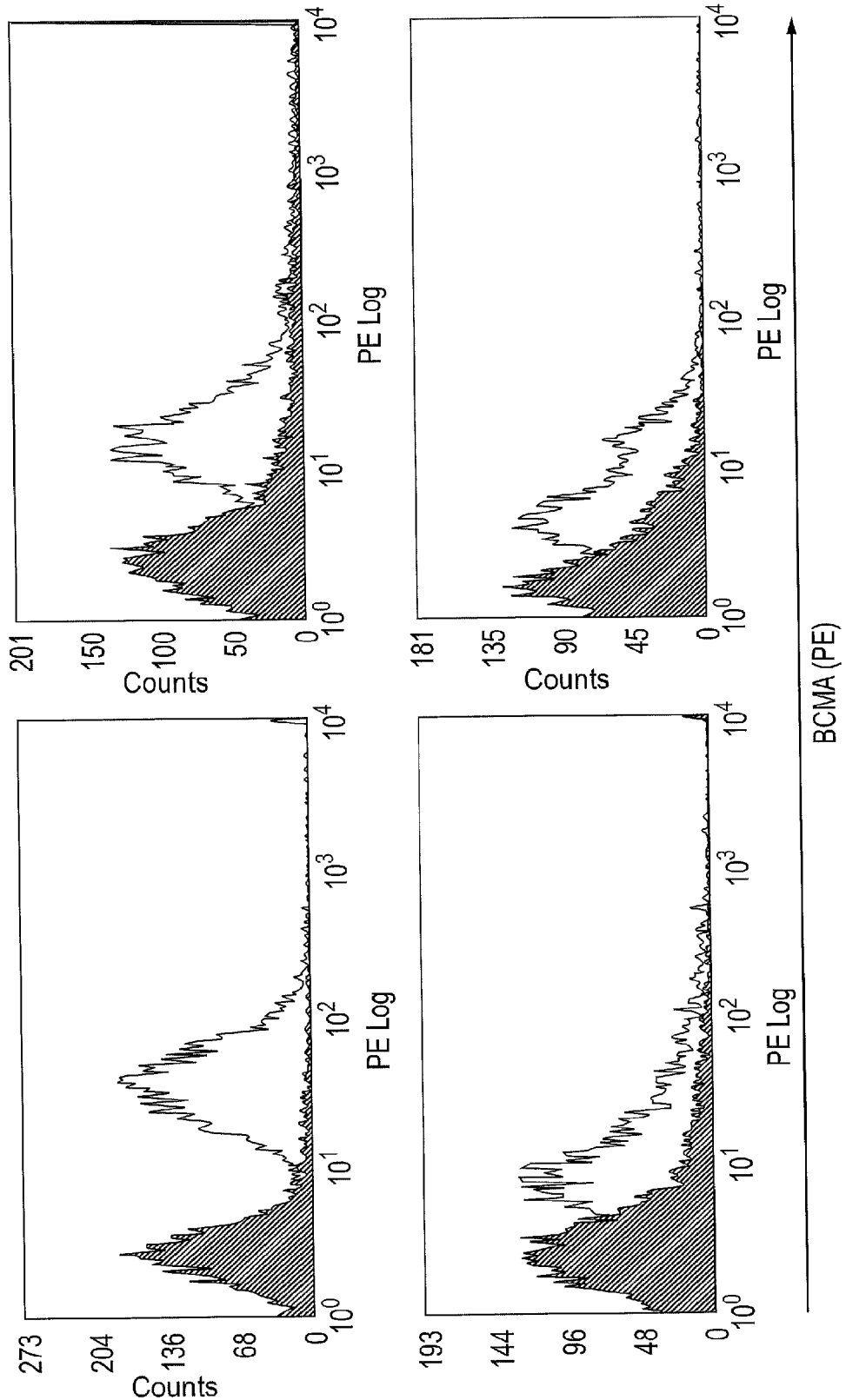

FIG. 14—Examples of BCMA expression on primary myelomas

Four examples of myeloma samples stained with the rat anti-human BCMA mAb Vicky1 is shown. The first panel shows bright BCMA staining in a patient with a plasma cell leukemia (an unusual, advanced and aggressive form of myeloma). The other three cases are clinically and morphologically typical myelomas. They show the intermediate or dim staining typically seen. Staining with isotype control (grey) is superimposed. These are examples of cumulative BCMA expression data shown in FIG. 2.

FIGS. 15A-15C—Amino acid sequence of APRIL-CARS with a V5 epitope tag.

FIG. 15A: dAPRIL-HCH2CH3pvaa-CD280XZ

FIG. 15B: dAPRIL-CD8STK-CD280XZ

FIG. 15C: dAPRIL-HNG-CD280XZ

Sequences in this figure differ from those in FIG. 5 have a different signal peptide and no V5 tag.

Figure 16:
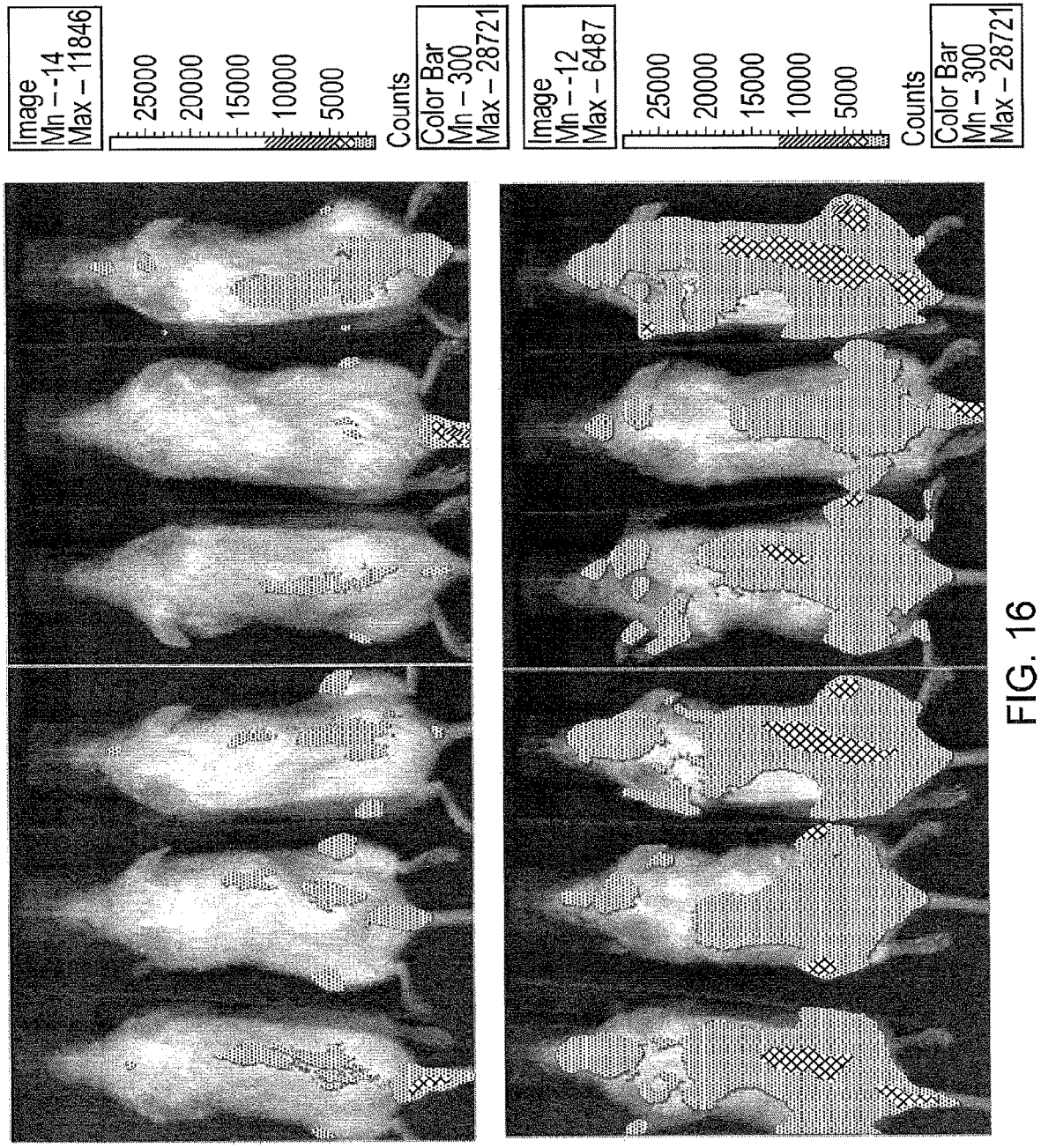
Figure 16:
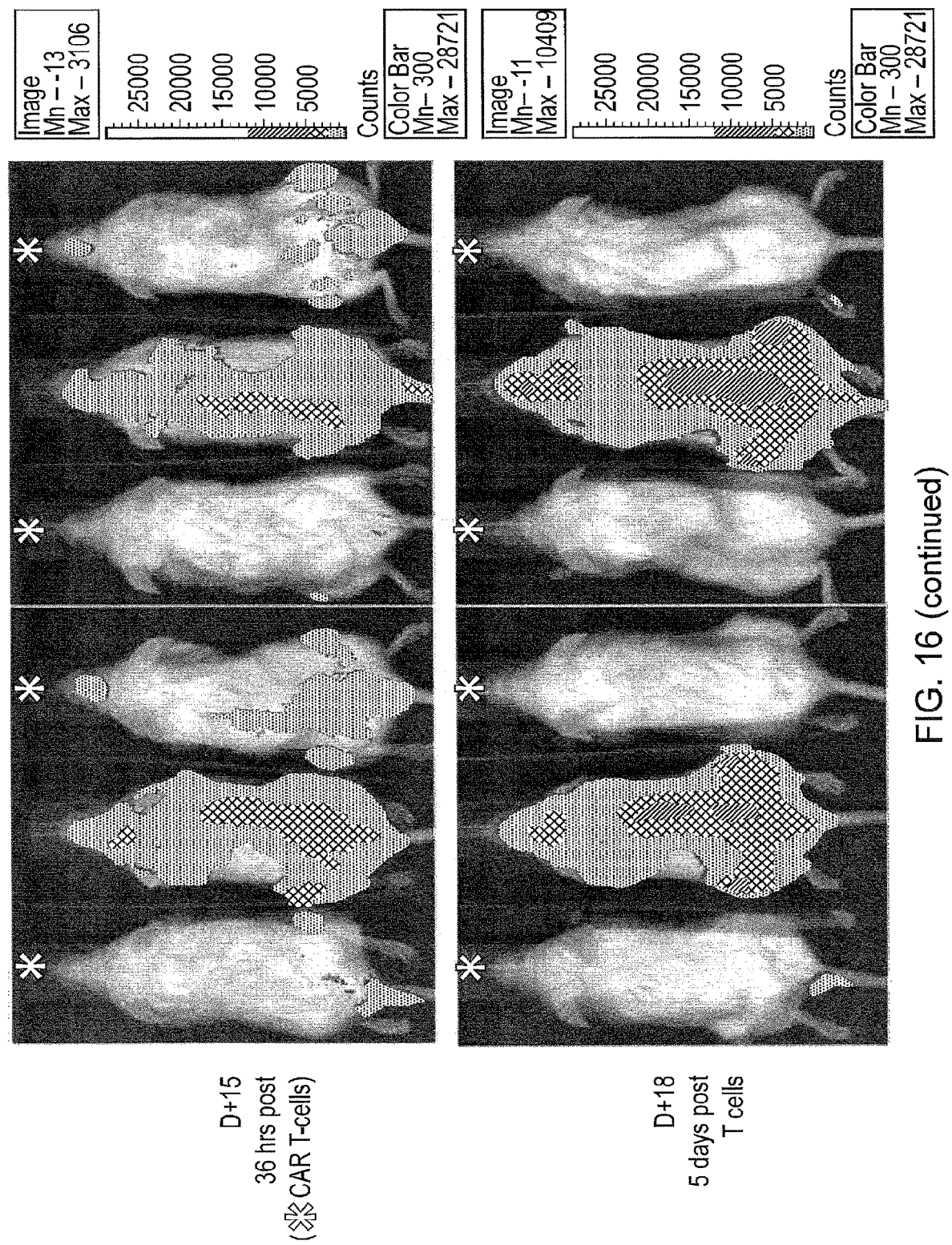

FIG. 16—Demonstration of in vivo function of APRIL CAR T-cells

Six 3 month old female NSG mice received $1 \times 10^7$ MM1.s.FLuc cells vial tail-vein injection. Mice were imaged with bioluminescence at day 8 and day 13. After imaging on day 13, four mice received 5×10⁶ APRIL CAR T-cells via tail vein injection. Mice were imaged on day 13 and day 18. Mice which received CAR T-cells are indicated with (*). Remission of Myeloma could be observed by Day 18 in all treated mice, while disease in untreated mice progressed.

SUMMARY OF ASPECTS OF THE INVENTION

B-cell membrane antigen (BCMA) is a surface protein expressed on nearly all Multiple Myeloma (MM). BCMA is only otherwise expressed on plasma cells hence targeting this antigen may prove an effective treatment of myeloma. However, the low-level expression of BCMA (See FIG. 2), is a consideration when targeting this antigen.

The present inventors have surprisingly found that if a binding domain is used based on A proliferation-inducing ligand (APRIL), rather than a BCMA-binding antibody, in a CAR-type molecule, T cells expressing such CARs cause very efficient killing of BCMA-expressing target cells, even those with low-levels of expression.

Without wishing to be bound by theory, the present inventors predict that this is because the three-fold symmetry inherent in the binding of BCMA with APRIL. This means that every interaction between the CAR and BCMA will involve 3 CARs, approximating 3 endodomains on the T-cell surface. Since T-cell activation is triggered by close approximation of signalling endodomains in an immunological synapse, the CAR design of the present invention is highly sensitive and specific. As BCMA is expressed at a very low density on primary myeloma cells (see FIGS. 2 and 7), this receptor design is particularly suited to this target.

Thus, in a first aspect the present invention provides a chimeric antigen receptor (CAR) comprising:
  (i) a B cell maturation antigen (BCMA)-binding domain which comprises at least part of a proliferation-inducing ligand (APRIL);
  (ii) a spacer domain
  (iii) a transmembrane domain; and
  (iv) an intracellular T cell signaling domain.

The BCMA-binding domain may comprise a truncated APRIL which comprises the BCMA binding site but lacks the amino terminal portion of APRIL responsible for proteoglycan binding. Such a molecule may comprise the sequence shown as SEQ ID No. 14. Alternatively the molecule may comprise a variant of that sequence having at least 80% sequence identity which binds BCMA.

The transmembrane and intracellular T-cell signalling domain may comprise the sequence shown as SEQ ID No. 7 or a variant thereof having at least 80% sequence identity.

The BCMA-binding domain and the transmembrane domain may be connected by a spacer. The spacer may comprise one of the following: a human IgG1 spacer; an IgG1 hinge; or a CD8 stalk.

The CAR of the first aspect of the invention may comprise the sequence shown as SEQ ID No. 1, 2, 3, 4, 5 or 6 or a variant thereof which has at least 80% sequence identity but retains the capacity to i) bind BCMA and ii) induce T cell signalling.

The CAR of the first aspect of the invention may bind to BCMA as a trimer.

In a second aspect, the present invention provides a nucleic acid sequence which encodes a CAR according to any preceding claim.

The nucleic acid sequence may comprise the sequence shown as SEQ ID No 15, 16, 17, 18, 19 or 20 or a variant thereof having at least 80% sequence identity.

In a third aspect, the present invention provides a vector which comprises a nucleic acid sequence according to the second aspect of the invention.

In a fourth aspect, the present invention provides a T cell or an NK cell which expresses a CAR according to the first aspect of the invention.

In a fifth aspect, the present invention provides a method for making a T cell or an NK cell according to the fourth aspect of the invention, which comprises the step of introducing a nucleic acid according to the second aspect of the invention into a T cell or an NK cell.

In a sixth aspect, the present invention provides a pharmaceutical composition which comprises a vector according to the third aspect of the invention or T cell/NK cell according to the fourth aspect of the invention, together with a pharmaceutically acceptable carrier, diluent or excipient.

In a seventh aspect, the present invention provides a method for treating a plasma cell disorder which comprises the step of administering a vector according to the third aspect of the invention or T cell/NK cell according to the fourth aspect of the invention to a subject.

The plasma cell disorder may be selected from plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance and smoldering multiple myeloma.

The plasma cell disorder may be multiple myeloma.

In an eighth aspect, the present invention provides a vector according to the third aspect of the invention or T cell/NK cell according to the fourth aspect of the invention for use in treating a plasma cell disorder.

In a ninth aspect, the present invention provides use of a vector according to the third aspect of the invention or T cell/NK cell according to the fourth aspect of the invention in the manufacture of a medicament for treating a plasma cell disorder.

DETAILED DESCRIPTION

Chimeric Antigen Receptors (CARS)

Chimeric antigen receptors (CARs), also known as chimeric T cell receptors, artificial T cell receptors and chimeric immunoreceptors, are engineered receptors, which graft an arbitrary specificity onto an immune effector cell. In a classical CAR (FIG. 3), the specificity of a monoclonal antibody is grafted on to a T cell or NK cell. CAR-encoding nucleic acids may be introduced into T cells or NK cells using, for example, retroviral vectors. In this way, a large number of cancer-specific T cells or NK cells can be generated for adoptive cell transfer. Early clinical studies of this approach have shown efficacy in some cancers, primarily when targeting the pan-B-cell antigen CD19 to treat B-cell malignancies.

The target-antigen binding domain of a CAR is commonly fused via a spacer and transmembrane domain to a signaling endodomain. When the CAR binds the target-antigen, this results in the transmission of an activating signal to the T-cell it is expressed on.

The CAR of the present invention comprises:
  (i) a B cell maturation antigen (BCMA)-binding domain which comprises at least part of a proliferation-inducing ligand (APRIL), which is discussed in more detail below;
  (ii) a spacer
  (iii) a transmembrane domain; and
  (iv) an intracellular T cell signaling domain The CAR of the present invention may comprise one of the following amino acid sequences:

```
(dAPRIL-HCH2CH3pvaa-CD280XZ)
                                          SEQ ID No. 1
METDTLLLWVLLLWVPGSTGSVLHLVPINATSKDDSDVTEVMWQPA
LRRGRGLQAQGYGVRIQDAGVYLLYSQVLFQDVTFTMGQVVSREGQ
GRQETLFRCIRSMPSHPDRAYNSCYSAGVFHLHQGDILSVIIPRAR
AKLNLSPHGTFLGFVKLSGGGSDPAEPKSPDKTHTCPPCPAPPVAG
PSVFLFPPKPKDTLMIARTPEVTCVVVDVSHEDPEVKFNWYVDGVE
VHNAKTKPREEQYNSTYRVVSVLTVLHQDWLNGKEYKCKVSNKALP
APIEKTISKAKGQPREPQVYTLPPSRDELTKNQVSLTCLVKGFYPS
DIAVEWESNGQPENNYKTTPPVLDSDGSFFLYSKLTVDKSRWQQGN
VFSCSVMHEALHNHYTQKSLSLSPGKKDPKFWVLVVVGGVLACYSL
LVTVAFIIFWVRSKRSRLLHSDYMNMTPRRPGPTRKHYQPYAPPRD
FAAYRSRDQRLPPDAHKPPGGGSFRTPIQEEQADAHSTLAKIRVKF
SRSADAPAYQQGQNQLYNELNLGRREEYDVLDKRRGRDPEMGGKPR
RKNPQEGLYNELQKDKMAEAYSEIGMKGERRRGKGHDGLYQGLSTA
TKDTYDALHMQALPPR (dAPRIL-CD8STK-CD280XZ)
                                          SEQ ID No. 2
METDTLLLWVLLLWVPGSTGSVLHLVPINATSKDDSDVTEVMWQPA
LRRGRGLQAQGYGVRIQDAGVYLLYSQVLFQDVTFTMGQVVSREGQ
GRQETLFRCIRSMPSHPDRAYNSCYSAGVFHLHQGDILSVIIPRAR
AKLNLSPHGTFLGFVKLSGGGSDPTTTPAPRPPTPAPTIASQPLSL
RPEACRPAAGGAVHTRGLDFACDIFWVLVVVGGVLACYSLLVTVAF
IIFWVRSKRSRLLHSDYMNMTPRRPGPTRKHYQPYAPPRDFAAYRS
RDQRLPPDAHKPPGGGSFRTPIQEEQADAHSTLAKIRVKFSRSADA
PAYQQGQNQLYNELNLGRREEYDVLDKRRGRDPEMGGKPRRKNPQE
GLYNELQKDKMAEAYSEIGMKGERRRGKGHDGLYQGLSTATKDTYD
ALHMQALPPR (dAPRIL-HNG-CD280XZ)
                                          SEQ ID No. 3
METDTLLLWVLLLWVPGSTGSVLHLVPINATSKDDSDVTEVMWQPA
LRRGRGLQAQGYGVRIQDAGVYLLYSQVLFQDVTFTMGQVVSREGQ
GRQETLFRCIRSMPSHPDRAYNSCYSAGVFHLHQGDILSVIIPRAR
AKLNLSPHGTFLGFVKLSGGGSDPAEPKSPDKTHTCPPCPKDPKFW
VLVVVGGVLACYSLLVTVAFIIFWVRSKRSRLLHSDYMNMTPRRPG
PTRKHYQPYAPPRDFAAYRSRDQRLPPDAHKPPGGGSFRTPIQEEQ
ADAHSTLAKIRVKFSRSADAPAYQQGQNQLYNELNLGRREEYDVLD
KRRGRDPEMGGKPRRKNPQEGLYNELQKDKMAEAYSEIGMKGERRR
GKGHDGLYQGLSTATKDTYDALHMQALPPR (dAPRIL-HCH2CH3pvaa-CD280XZ)
                                          SEQ ID No. 4
MGTSLLCWMALCLLGADHADGKPIPNPLLGLDSTSGGGGSVLHLVP
INATSKDDSDVTEVMWQPALRRGRGLQAQGYGVRIQDAGVYLLYSQ
VLFQDVTFTMGQVVSREGQGRQETLFRCIRSMPSHPDRAYNSCYSA
GVFHLHQGDILSVIIPRARAKLNLSPHGTFLGFVKLSGGGSDPAEP
KSPDKTHTCPPCPAPPVAGPSVFLFPPKPKDTLMIARTPEVTCVVV
DVSHEDPEVKFNWYVDGVEVHNAKTKPREEQYNSTYRVVSVLTVLH
QDWLNGKEYKCKVSNKALPAPIEKTISKAKGQPREPQVYTLPPSRD
ELTKNQVSLTCLVKGFYPSDIAVEWESNGQPENNYKTTPPVLDSDG
SFFLYSKLTVDKSRWQQGNVFSCSVMHEALHNHYTQKSLSLSPGKK
DPKFWVLVVVGGVLACYSLLVTVAFIIFWVRSKRSRLLHSDYMNMT
PRRPGPTRKHYQPYAPPRDFAAYRSRDQRLPPDAHKPPGGGSFRTP
IQEEQADAHSTLAKIRVKFSRSADAPAYQQGQNQLYNELNLGRREE
YDVLDKRRGRDPEMGGKPRRKNPQEGLYNELQKDKMAEAYSEIGMK
GERRRGKGHDGLYQGLSTATKDTYDALHMQALPPR (dAPRIL-CD8STK-CD280XZ)
                                          SEQ ID No. 5
MGTSLLCWMALCLLGADHADGKPIPNPLLGLDSTSGGGGSVLHLVP
INATSKDDSDVTEVMWQPALRRGRGLQAQGYGVRIQDAGVYLLYSQ
VLFQDVTFTMGQVVSREGQGRQETLFRCIRSMPSHPDRAYNSCYSA
GVFHLHQGDILSVIIPRARAKLNLSPHGTFLGFVKLSGGGSDPTTT
PAPRPPTPAPTIASQPLSLRPEACRPAAGGAVHTRGLDFACDIFWV
LVVVGGVLACYSLLVTVAFIIFWVRSKRSRLLHSDYMNMTPRRPGP
TRKHYQPYAPPRDFAAYRSRDQRLPPDAHKPPGGGSFRTPIQEEQA
DAHSTLAKIRVKFSRSADAPAYQQGQNQLYNELNLGRREEYDVLDK
RRGRDPEMGGKPRRKNPQEGLYNELQKDKMAEAYSEIGMKGERRRG
KGHDGLYQGLSTATKDTYDALHMQALPPR (dAPRIL-HNG-CD280XZ)
                                          SEQ ID No. 6
MGTSLLCWMALCLLGADHADGKPIPNPLLGLDSTSGGGGSVLHLVP
INATSKDDSDVTEVMWQPALRRGRGLQAQGYGVRIQDAGVYLLYSQ
VLFQDVTFTMGQVVSREGQGRQETLFRCIRSMPSHPDRAYNSCYSA
GVFHLHQGDILSVIIPRARAKLNLSPHGTFLGFVKLSGGGSDPAEP
KSPDKTHTCPPCPKDPKFWVLVVVGGVLACYSLLVTVAFIIFWVRS
KRSRLLHSDYMNMTPRRPGPTRKHYQPYAPPRDFAAYRSRDQRLPP
DAHKPPGGGSFRTPIQEEQADAHSTLAKIRVKFSRSADAPAYQQGQ
NQLYNELNLGRREEYDVLDKRRGRDPEMGGKPRRKNPQEGLYNELQ
KDKMAEAYSEIGMKGERRRGKGHDGLYQGLSTATKDTYDALHMQAL
PPR
```

The molecule of the invention may comprise a variant of the sequence shown as SEQ ID No. 1, 2, 3, 4, 5 or 6 having at least 80, 85, 90, 95, 98 or 99% sequence identity, provided that the variant sequence is a molecule as defined in the first aspect of the invention, i.e. a CAR which comprises:

(i) a BCMA-binding domain;
(ii) a spacer domain
(iii) a transmembrane domain; and
(iv) an intracellular T cell signaling domain.

The percentage identity between two polypeptide sequences may be readily determined by programs such as BLAST which is freely available at http://blast.ncbi.nlm.nih.gov.

Transmembrane Domain

The transmembrane domain is the sequence of the CAR that spans the membrane. It may comprise a hydrophobic alpha helix. The transmembrane domain may be derived from CD28, which gives good receptor stability. The transmembrane domain may be derived from any type I transmembrane protein. The transmembrane domain may be a synthetic sequence predicted to form a hydrophobic helix.

Intracellular T Cell Signaling Domain (Endodomain)

The endodomain is the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together (Pule et al, Molecular therapy, 2005: Volume 12; Issue 5; Pages 933-41). The CAR endodomain may also be derived from other signaling domains either individually or in combination, derived from signaling proteins found in nature or artificial ones constructed by those skilled in the art such that the CAR transmits a suitable signal to for an effective CAR therapeutic.

The endodomain of the CAR of the present invention may comprise the CD28 endodomain and OX40 and CD3-Zeta endodomain.

The transmembrane and intracellular T-cell signalling domain (endodomain) of the CAR of the present invention may comprise the sequence shown as SEQ ID No. 7 or a variant thereof having at least 80% sequence identity.

```
                                        SEQ ID No. 7
FWVLVVVGGVLACYSLLVTVAFIIFWVRSKRSRLLHSDYMNMTPRR

PGPTRKHYQPYAPPRDFAAYRSRDQRLPPDAHKPPGGGSFRTPIQE

EQADAHSTLAKIRVKFSRSADAPAYQQGQNQLYNELNLGRREEYDV

LDKRRGRDPEMGGKPRRKNPQEGLYNELQKDKMAEAYSEIGMKGER

RRGKGHDGLYQGLSTATKDTYDALHMQALPPR
```

A variant sequence may have at least 80%, 85%, 90%, 95%, 98% or 99% sequence identity to SEQ ID No. 7, provided that the sequence provides an effective transmembrane domain and an effective intracellular T cell signaling domain.

Signal Peptide

The CAR of the present invention may comprise a signal peptide so that when the CAR is expressed inside a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The CAR of the invention may have the general formula:
Signal peptide—BCMA-binding domain spacer domain—transmembrane domain—intracellular T cell signaling domain.

The signal peptide may comprise the SEQ ID No. 8 or 9 or a variant thereof having 5, 4, 3, 2 or 1 amino acid mutations (insertions, substitutions or additions) provided that the signal peptide still functions to cause cell surface expression of the CAR.

```
SEQ ID No. 8:
MGTSLLCWMALCLLGADHADG

SEQ ID No. 9:
METDTLLLWVLLLWVPGSTG
```

The signal peptide of SEQ ID No. 8 and SEQ ID No 9 is compact and highly efficient. It is predicted to give about 95% cleavage after the terminal glycine, giving efficient removal by signal peptidase.

Spacer

The CAR of the present invention may comprise a spacer sequence to connect the BCMA-binding domain with the transmembrane domain and spatially separate the BCMA-binding domain from the endodomain. A flexible spacer allows to the BCMA-binding domain to orient in different directions to enable BCMA binding.

The spacer sequence may, for example, comprise an IgG1 Fc region, an IgG1 hinge or a CD8 stalk. The linker may alternatively comprise an alternative linker sequence which has similar length and/or domain spacing properties as an IgG1 Fc region, an IgG1 hinge or a CD8 stalk.

The spacer may be a short spacer, for example a spacer which comprises less than 100, less than 80, less than 60 or less than 45 amino acids. The spacer may be or comprise an IgG1 hinge or a CD8 stalk or a modified version thereof.

A human IgG1 spacer may be altered to remove Fc binding motifs.

Examples of amino acid sequences for these spacers are given below:

```
(hinge-CH2CH3 of human IgG1)
                                       SEQ ID No. 10
AEPKSPDKTHTCPPCPAPPVAGPSVFLFPPKPKDTLMIARTPEVTC

VVVDVSHEDPEVKFNWYVDGVEVHNAKTKPREEQYNSTYRVVSVLT

VLHQDWLNGKEYKCKVSNKALPAPIEKTISKAKGQPREPQVYTLPP

SRDELTKNQVSLTCLVKGFYPSDIAVEWESNGQPENNYKTTPPVLD

SDGSFFLYSKLTVDKSRWQQGNVFSCSVMHEALHNHYTQKSLSLSP

GKKD

SEQ ID No. 11 (human CD8 stalk):
TTTPAPRPPTPAPTIASQPLSLRPEACRPAAGGAVHTRGLDFACDI

SEQ ID No. 12 (human IgG1 hinge):
AEPKSPDKTHTCPPCPKDPK
```

B-Cell Membrane Antigen (BCMA)

The CAR of the first aspect of the invention comprises a domain which binds BCMA.

BCMA, also known as TNFRSF17, is a plasma cell specific surface antigen which is expressed exclusively on B-lineage haemopoietic cells or dendritic cells. It is a member of the TNF receptor family. BCMA is not expressed on naïve B cells but is up-regulated during B-cell differentiation into plasmablasts, and is brightly expressed on memory B cells, plasmablasts and bone marrow plasma cells. BCMA is also expressed on the majority of primary myeloma cells. Unlike other CAR targets such as CD19, BCMA is expressed at low density (FIG. 2).

Figure 1:
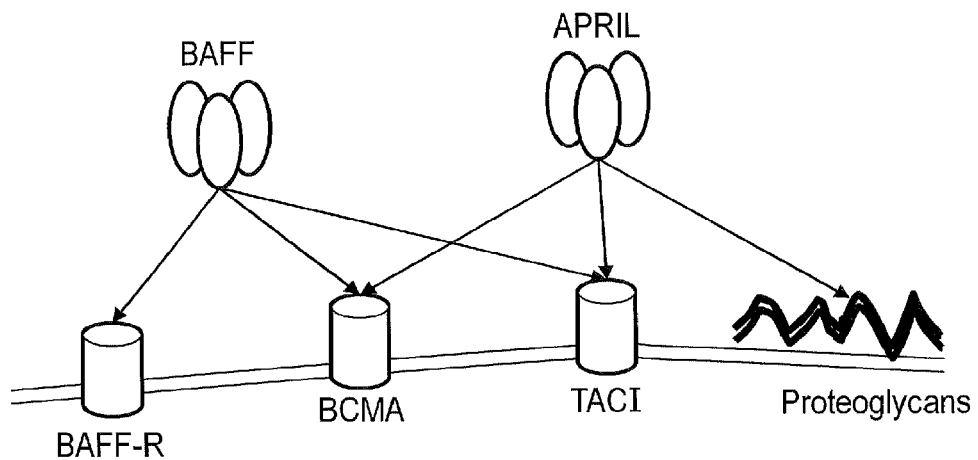
FIG. 1—Ligand Specificity and Function Assignment of APRIL and BAFF

BCMA functions within a network of interconnected ligands and receptors which is shown schematically in FIG. 1. Two other TNF receptors share the ligands APRIL and BAFF with BCMA-TACI (TNFRSF13B), which is found on activated T-cells and all B-cells and BAFF-R (TNFRSF13C) which is predominantly expressed on B-lymphocytes. Multiple myeloma cells express TACI in some cases and BCMA in most cases, but never BAFF-R.

APRIL

The BCMA-binding domain of the CAR of the invention and comprises at least part of a proliferation-inducing ligand (APRIL). APRIL is also known as TNFSF13.

The wild-type sequence of APRIL is available at UNIPROT/O75888 and is show below (SEQ ID No. 13). It is not a classical secreted protein in that it has no signal peptide. It has a furin cleavage site "KQKKQK" (underlined in SEQ ID No. 13). The amino terminus is involved in proteoglycan binding.

The BCMA-binding domain may comprise the BCMA-binding site of APRIL. The BCMA-binding domain may comprise a fragment of APRIL which comprises the BCMA-binding site.

The BCMA-binding domain may comprise a truncated APRIL, which lacks the amino terminal end of the molecule. The truncated APRIL may retain BCMA and TACI binding but lose proteoglycan binding. Truncated APRIL can be cleaved at or immediately after the furin cleavage site. Truncated APRIL may lack the amino terminal 116 amino acids from the wild-type APRIL molecule shown as SEQ ID No. 13. Truncated APRIL may comprise the sequence shown as SEQ ID No. 14 (which corresponds to the portion of SEQ ID No. 13 shown in bold) or a variant thereof. This corresponds to the portion of the molecule which is needed for BCMA and TACI binding.

```
                                      SEQ ID No. 13
         10          20          30          40
    MPASSPFLLA  PKGPPGNMGG  PVREPALSVA  LWLSWGAALG 50          60          70          80
    AVACAMALLT  QQTELQSLRR  EVSRLQGTGG  PSQNGEGYPW 90         100         110         120
    QSLPEQSSDA  LEAWENGERS  RKRRAVLTQK  QKKQHSVLHL 130         140         150         160
    VPINATSKDD  SDVTEVMWQP  ALRRGRGLQA  QGYGVRIQDA 170         180         190         200
    GVYLLYSQVL  FQDVTFTMGQ  VVSREGQGRQ  ETLFRCIRSM 210         220         230         240
    PSHPDRAYNS  CYSAGVFHLH  QGDILSVIIP  RARAKLNLSP

250
    HGTFLGFVKL
```

```
                                      SEQ ID No. 14
    VLHLVPINATSKDDSDVTEVMWQPALRRGRGLQAQGYGVRIQDAGV

YLLYSQVLFQDVTFTMGQVVSREGQGRQETLFRCIRSMPSHPDRAY

NSCYSAGVFHLHQGDILSVIIPRARAKLNLSPHGTFLGFVKL
```

The CAR of the present invention may comprise a variant of the truncated APRIL molecule shown as SEQ ID No. 14 which has at least 80% amino acid sequence identity and which has the same or improved BCMA binding capabilities. The variant sequence may have at least 80%, 85%, 90%, 95%, 98% or 99% sequence identity to SEQ ID No. 14.

Nucleic Acid Sequence

The second aspect of the invention relates to a nucleic acid sequence which codes for a CAR of the first aspect of the invention.

The nucleic acid sequence may be or comprise one of the following sequences:

```
(dAPRIL-HCH2CH3pvaa-CD28OXZ)
                                      SEQ ID No. 15
ATGGAGACCGACACCCTGCTGCTGTGGGTGCTGCTGCTGTGGGTGC

CAGGCAGCACCGGCAGCGTGCTCCACCTGGTGCCCATCAACGCCAC

CAGCAAGGACGACTCTGATGTGACCGAGGTGATGTGGCAGCCAGCC

CTGAGACGGGGCAGAGGCCTGCAGGCCCAGGGCTACGGCGTGAGAA

TCCAGGACGCTGGCGTGTACCTGCTGTACTCCCAGGTGCTGTTCCA

GGACGTGACCTTCACAATGGGCCAGGTGGTGAGCCGGGAGGGCCAG

GGCAGACAGGAGACCCTGTTCCGGTGCATCCGGAGCATGCCCAGCC

ACCCCGACAGAGCCTACAACAGCTGCTACAGCGCTGGCGTGTTTCA

CCTGCACCAGGGCGACATCCTGAGCGTGATCATCCCCAGAGCCAGA

GCCAAGCTGAACCTGTCCCCCCACGGCACCTTTCTGGGCTTCGTGA

AGCTGTCTGGAGGCGGCTCGGATCCCGCCGAGCCCAAATCTCCTGA

CAAAACTCACACATGCCCACCGTGCCCAGCACCTCCCGTGGCCGGC

CCGTCAGTCTTCCTCTTCCCCCCAAAACCCAAGGACACCCTCATGA

TCGCCCGGACCCCTGAGGTCACATGCGTGGTGGTGGACGTGAGCCA

CGAAGACCCTGAGGTCAAGTTCAACTGGTACGTGGACGGCGTGGAG

GTGCATAATGCCAAGACAAAGCCGCGGGAGGAGCAGTACAACAGCA

CGTACCGTGTGGTCAGCGTCCTCACCGTCCTGCACCAGGACTGGCT

GAATGGCAAGGAGTACAAGTGCAAGGTCTCCAACAAAGCCCTCCCA

GCCCCCATCGAGAAAACCATCTCCAAAGCCAAAGGGCAGCCCCGAG

AACCACAGGTGTACACCCTGCCCCCATCCCGGGATGAGCTGACCAA

GAACCAGGTCAGCCTGACCTGCCTGGTCAAAGGCTTCTATCCCAGC

GACATCGCCGTGGAGTGGGAGAGCAATGGGCAACCGGAGAACAACT

ACAAGACCACGCCTCCCGTGCTGGACTCCGACGGCTCCTTCTTCCT

CTACAGCAAGCTCACCGTGGACAAGAGCAGGTGGCAGCAGGGGAAC

GTCTTCTCATGCTCCGTGATGCATGAGGCTCTGCACAACCACTACA

CGCAGAAGAGCCTCTCCCTGTCTCCGGGTAAAAAAGATCCCAAATT
```

-continued
```
TTGGGTGCTGGTGGTGGTTGGTGGAGTCCTGGCTTGCTATAGCTTG

CTAGTAACAGTGGCCTTTATTATTTTCTGGGTGAGGAGTAAGAGGA

GCAGGCTCCTGCACAGTGACTACATGAACATGACTCCCCGCCGCCC

CGGGCCCACCCGCAAGCATTACCAGCCCTATGCCCCACCACGCGAC

TTCGCAGCCTATCGCTCCAGGGACCAGAGGCTGCCCCCCGATGCCC

ACAAGCCCCCTGGGGGAGGCAGTTTCCGGACCCCCATCCAAGAGGA

GCAGGCCGACGCCCACTCCACCCTGGCCAAGATCAGAGTGAAGTTC

AGCAGGAGCGCAGACGCCCCCGCGTACCAGCAGGGCCAGAACCAGC

TCTATAACGAGCTCAATCTAGGACGAAGAGAGGAGTACGATGTTTT

GGACAAGAGACGTGGCCGGGACCCTGAGATGGGGGAAAGCCGAGA

AGGAAGAACCCTCAGGAAGGCCTGTACAATGAACTGCAGAAAGATA

AGATGGCGGAGGCCTACAGTGAGATTGGGATGAAAGGCGAGCGCCG

GAGGGGCAAGGGGCACGATGGCCTTTACCAGGGTCTCAGTACAGCC

ACCAAGGACACCTACGACGCCCTTCACATGCAGGCCCTGCCTCCTC

GCTAA
```
(dAPRIL-CD8STK-CD280XZ)
SEQ ID No. 16
```
ATGGAGACCGACACCCTGCTGCTGTGGGTGCTGCTGCTGTGGGTGC

CAGGCAGCACCGGCAGCGTGCTCCACCTGGTGCCCATCAACGCCAC

CAGCAAGGACGACTCTGATGTGACCGAGGTGATGTGGCAGCCAGCC

CTGAGACGGGCAGAGGCCTGCAGGCCCAGGGCTACGGCGTGAGAA

TCCAGGACGCTGGCGTGTACCTGCTGTACTCCCAGGTGCTGTTCCA

GGACGTGACCTTCACAATGGGCCAGGTGGTGAGCCGGGAGGGCCAG

GGCAGACAGGAGACCCTGTTCCGGTGCATCCGGAGCATGCCCAGCC

ACCCCGACAGAGCCTACAACAGCTGCTACAGCGCTGGCGTGTTTCA

CCTGCACCAGGGCGACATCCTGAGCGTGATCATCCCCAGAGCCAGA

GCCAAGCTGAACCTGTCCCCCACGGCACCTTTCTGGGCTTCGTGA

AGCTGTCTGGAGGCGGCTCGGATCCCACCACGACGCCAGCGCCGCG

ACCACCAACACCGGCGCCCACCATCGCGTCGCAGCCCCTGTCCCTG

CGCCCAGAGGCGTGCCGGCCAGCGGCGGGGGCGCAGTGCACACGA

GGGGGCTGGACTTCGCCTGTGATATCTTTTGGGTGCTGGTGGTGGT

TGGTGGAGTCCTGGCTTGCTATAGCTTGCTAGTAACAGTGGCCTTT

ATTATTTTCTGGGTGAGGAGTAAGAGGAGCAGGCTCCTGCACAGTG

ACTACATGAACATGACTCCCCGCCGCCCCGGGCCCACCCGCAAGCA

TTACCAGCCCTATGCCCCACCACGCGACTTCGCAGCCTATCGCTCC

AGGGACCAGAGGCTGCCCCCCGATGCCCACAAGCCCCCTGGGGGAG

GCAGTTTCCGGACCCCCATCCAAGAGGAGCAGGCCGACGCCCACTC

CACCCTGGCCAAGATCAGAGTGAAGTTCAGCAGGAGCGCAGACGCC

CCCGCGTACCAGCAGGGCCAGAACCAGCTCTATAACGAGCTCAATC

TAGGACGAAGAGAGGAGTACGATGTTTTGGACAAGAGACGTGGCCG

GGACCCTGAGATGGGGGAAAGCCGAGAAGGAAGAACCCTCAGGAA

GGCCTGTACAATGAACTGCAGAAAGATAAGATGGCGGAGGCCTACA

GTGAGATTGGGATGAAAGGCGAGCGCCGGAGGGGCAAGGGGCACGA

TGGCCTTTACCAGGGTCTCAGTACAGCCACCAAGGACACCTACGAC

GCCCTTCACATGCAGGCCCTGCCTCCTCGCTAA
```
(dAPRIL-HNG-CD280XZ)
SEQ ID No. 17
```
ATGGAGACCGACACCCTGCTGCTGTGGGTGCTGCTGCTGTGGGTGC

CAGGCAGCACCGGCAGCGTGCTCCACCTGGTGCCCATCAACGCCAC

CAGCAAGGACGACTCTGATGTGACCGAGGTGATGTGGCAGCCAGCC

CTGAGACGGGCAGAGGCCTGCAGGCCCAGGGCTACGGCGTGAGAA

TCCAGGACGCTGGCGTGTACCTGCTGTACTCCCAGGTGCTGTTCCA

GGACGTGACCTTCACAATGGGCCAGGTGGTGAGCCGGGAGGGCCAG

GGCAGACAGGAGACCCTGTTCCGGTGCATCCGGAGCATGCCCAGCC

ACCCCGACAGAGCCTACAACAGCTGCTACAGCGCTGGCGTGTTTCA

CCTGCACCAGGGCGACATCCTGAGCGTGATCATCCCCAGAGCCAGA

GCCAAGCTGAACCTGTCCCCCACGGCACCTTTCTGGGCTTCGTGA

AGCTGTCTGGAGGCGGCTCGGATCCCGCCGAGCCCAAATCTCCTGA

CAAAACTCACACATGCCCACCGTGCCCAAAAGATCCCAAATTTTGG

GTGCTGGTGGTGGTTGGTGGAGTCCTGGCTTGCTATAGCTTGCTAG

TAACAGTGGCCTTTATTATTTTCTGGGTGAGGAGTAAGAGGAGCAG

GCTCCTGCACAGTGACTACATGAACATGACTCCCCGCCGCCCCGGG

CCCACCCGCAAGCATTACCAGCCCTATGCCCCACCACGCGACTTCG

CAGCCTATCGCTCCAGGGACCAGAGGCTGCCCCCCGATGCCCACAA

GCCCCCTGGGGGAGGCAGTTTCCGGACCCCCATCCAAGAGGAGCAG

GCCGACGCCCACTCCACCCTGGCCAAGATCAGAGTGAAGTTCAGCA

GGAGCGCAGACGCCCCCGCGTACCAGCAGGGCCAGAACCAGCTCTA

TAACGAGCTCAATCTAGGACGAAGAGAGGAGTACGATGTTTTGGAC

AAGAGACGTGGCCGGGACCCTGAGATGGGGGAAAGCCGAGAAGGA

AGAACCCTCAGGAAGGCCTGTACAATGAACTGCAGAAAGATAAGAT

GGCGGAGGCCTACAGTGAGATTGGGATGAAAGGCGAGCGCCGGAGG

GGCAAGGGGCACGATGGCCTTTACCAGGGTCTCAGTACAGCCACCA

AGGACACCTACGACGCCCTTCACATGCAGGCCCTGCCTCCTCGCTA

A
```
(dAPRIL-HCH2CH3pvaa-CD280XZ)
SEQ ID No. 18
```
ATGGGCACCTCCCTGCTGTGCTGGATGGCCCTGTGCCTGCTGGGAG

CCGACCACGCCGACGGCAAGCCCATTCCCAACCCCCTGCTGGGCCT

GGACTCCACCTCTGGCGAGGCGGCAGCGTGCTGCACCTGGTGCCC

ATCAACGCCACCAGCAAGGACGACTCTGATGTGACCGAGGTGATGT

GGCAGCCAGCCCTGAGACGGGCAGAGGCCTGCAGGCCCAGGGCTA

CGGCGTGAGAATCCAGGACGCTGGCGTGTACCTGCTGTACTCCCAG

GTGCTGTTCCAGGACGTGACCTTCACAATGGGCCAGGTGGTGAGCC

GGGAGGGCCAGGGCAGACAGGAGACCCTGTTCCGGTGCATCCGGAG
```

CATGCCCAGCCACCCCGACAGAGCCTACAACAGCTGCTACAGCGCT

GGCGTGTTTCACCTGCACCAGGGCGACATCCTGAGCGTGATCATCC

CCAGAGCCAGAGCCAAGCTGAACCTGTCCCCCACGGCACCTTTCT

GGGCTTCGTGAAGCTGTCTGGAGGCGGCTCGGATCCCGCCGAGCCC

AAATCTCCTGACAAAACTCACACATGCCCACCGTGCCCAGCACCTC

CCGTGGCCGGCCCGTCAGTCTTCCTCTTCCCCCCAAAACCCAAGGA

CACCCTCATGATCGCCCGGACCCCTGAGGTCACATGCGTGGTGGTG

GACGTGAGCCACGAAGACCCTGAGGTCAAGTTCAACTGGTACGTGG

ACGGCGTGGAGGTGCATAATGCCAAGACAAAGCCGCGGGAGGAGCA

GTACAACAGCACGTACCGTGTGGTCAGCGTCCTCACCGTCCTGCAC

CAGGACTGGCTGAATGGCAAGGAGTACAAGTGCAAGGTCTCCAACA

AAGCCCTCCCAGCCCCCATCGAGAAAACCATCTCCAAAGCCAAAGG

GCAGCCCCGAGAACCACAGGTGTACACCCTGCCCCCATCCCGGGAT

GAGCTGACCAAGAACCAGGTCAGCCTGACCTGCCTGGTCAAAGGCT

TCTATCCCAGCGACATCGCCGTGGAGTGGGAGAGCAATGGGCAACC

GGAGAACAACTACAAGACCACGCCTCCCGTGCTGGACTCCGACGGC

TCCTTCTTCCTCTACAGCAAGCTCACCGTGGACAAGAGCAGGTGGC

AGCAGGGGAACGTCTTCTCATGCTCCGTGATGCATGAGGCTCTGCA

CAACCACTACACGCAGAAGAGCCTCTCCCTGTCTCCGGGTAAAAAA

GATCCCAAATTTTGGGTGCTGGTGGTGGTTGGTGGAGTCCTGGCTT

GCTATAGCTTGCTAGTAACAGTGGCCTTTATTATTTTCTGGGTGAG

GAGTAAGAGGAGCAGGCTCCTGCACAGTGACTACATGAACATGACT

CCCCGCCGCCCGGGCCCACCCGCAAGCATTACCAGCCCTATGCCC

CACCACGCGACTTCGCAGCCTATCGCTCCAGGGACCAGAGGCTGCC

CCCCGATGCCCACAAGCCCCCTGGGGAGGCAGTTTCCGGACCCCC

ATCCAAGAGGAGCAGGCCGACGCCCACTCCACCCTGGCCAAGATCA

GAGTGAAGTTCAGCAGGAGCGCAGACGCCCCCGCGTACCAGCAGG

CCAGAACCAGCTCTATAACGAGCTCAATCTAGGACGAAGAGAGGAG

TACGATGTTTTGGACAAGAGACGTGGCCGGGACCCTGAGATGGGGG

GAAAGCCGAGAAGGAAGAACCCTCAGGAAGGCCTGTACAATGAACT

GCAGAAAGATAAGATGGCGGAGGCCTACAGTGAGATTGGGATGAAA

GGCGAGCGCCGGAGGGGCAAGGGGCACGATGGCCTTTACCAGGGTC

TCAGTACAGCCACCAAGGACACCTACGACGCCCTTCACATGCAGGC

CCTGCCTCCTCGCTAA (dAPRIL-CD8STK-CD280XZ)
SEQ ID No. 19
ATGGGCACCTCCCTGCTGTGCTGGATGGCCCTGTGCCTGCTGGGAG

CCGACCACGCCGACGGCAAGCCCATTCCCAACCCCCTGCTGGGCCT

GGACTCCACCTCTGGCGGAGGCGGCAGCGTGCTGCACCTGGTGCCC

ATCAACGCCACCAGCAAGGACGACTCTGATGTGACCGAGGTGATGT

GGCAGCCAGCCCTGAGACGGGGCAGAGGCCTGCAGGCCCAGGGCTA

CGGCGTGAGAATCCAGGACGCTGGCGTGTACCTGCTGTACTCCCAG

GTGCTGTTCCAGGACGTGACCTTCACAATGGGCCAGGTGGTGAGCC

GGGAGGGCCAGGGCAGACAGGAGACCCTGTTCCGGTGCATCCGGAG

CATGCCCAGCCACCCCGACAGAGCCTACAACAGCTGCTACAGCGCT

GGCGTGTTTCACCTGCACCAGGGCGACATCCTGAGCGTGATCATCC

CCAGAGCCAGAGCCAAGCTGAACCTGTCCCCCACGGCACCTTTCT

GGGCTTCGTGAAGCTGTCTGGAGGCGGCTCGGATCCCACCACGACG

CCAGCGCCGCGACCACCAACACCGGCGCCCACCATCGCGTCGCAGC

CCCTGTCCCTGCGCCCAGAGGCGTGCCGGCCAGCGGCGGGGGCGC

AGTGCACACGAGGGGGCTGGACTTCGCCTGTGATATCTTTTGGGTG

CTGGTGGTGGTTGGTGGAGTCCTGGCTTGCTATAGCTTGCTAGTAA

CAGTGGCCTTTATTATTTTCTGGGTGAGGAGTAAGAGGAGCAGGCT

CCTGCACAGTGACTACATGAACATGACTCCCCGCCGCCCCGGGCCC

ACCCGCAAGCATTACCAGCCCTATGCCCCACCACGCGACTTCGCAG

CCTATCGCTCCAGGGACCAGAGGCTGCCCCCCGATGCCCACAAGCC

CCCTGGGGAGGCAGTTTCCGGACCCCCATCCAAGAGGAGCAGGCC

GACGCCCACTCCACCCTGGCCAAGATCAGAGTGAAGTTCAGCAGGA

GCGCAGACGCCCCCGCGTACCAGCAGGGCCAGAACCAGCTCTATAA

CGAGCTCAATCTAGGACGAAGAGAGGAGTACGATGTTTTGGACAAG

AGACGTGGCCGGGACCCTGAGATGGGGGAAAGCCGAGAAGGAAGA

ACCCTCAGGAAGGCCTGTACAATGAACTGCAGAAAGATAAGATGGC

GGAGGCCTACAGTGAGATTGGGATGAAAGGCGAGCGCCGGAGGGGC

AAGGGGCACGATGGCCTTTACCAGGGTCTCAGTACAGCCACCAAGG

ACACCTACGACGCCCTTCACATGCAGGCCCTGCCTCCTCGCTAA (dAPRIL-HNG-CD280XZ)
SEQ ID No. 20
ATGGGCACCTCCCTGCTGTGCTGGATGGCCCTGTGCCTGCTGGGAG

CCGACCACGCCGACGGCAAGCCCATTCCCAACCCCCTGCTGGGCCT

GGACTCCACCTCTGGCGGAGGCGGCAGCGTGCTGCACCTGGTGCCC

ATCAACGCCACCAGCAAGGACGACTCTGATGTGACCGAGGTGATGT

GGCAGCCAGCCCTGAGACGGGGCAGAGGCCTGCAGGCCCAGGGCTA

CGGCGTGAGAATCCAGGACGCTGGCGTGTACCTGCTGTACTCCCAG

GTGCTGTTCCAGGACGTGACCTTCACAATGGGCCAGGTGGTGAGCC

GGGAGGGCCAGGGCAGACAGGAGACCCTGTTCCGGTGCATCCGGAG

CATGCCCAGCCACCCCGACAGAGCCTACAACAGCTGCTACAGCGCT

GGCGTGTTTCACCTGCACCAGGGCGACATCCTGAGCGTGATCATCC

CCAGAGCCAGAGCCAAGCTGAACCTGTCCCCCACGGCACCTTTCT

GGGCTTCGTGAAGCTGTCTGGAGGCGGCTCGGATCCCGCCGAGCCC

AAATCTCCTGACAAAACTCACACATGCCCACCGTGCCCAAAAGATC

CCAAATTTTGGGTGCTGGTGGTGGTTGGTGGAGTCCTGGCTTGCTA

TAGCTTGCTAGTAACAGTGGCCTTTATTATTTTCTGGGTGAGGAGT

AAGAGGAGCAGGCTCCTGCACAGTGACTACATGAACATGACTCCCC

-continued
```
GCCGCCCCGGGCCCACCCGCAAGCATTACCAGCCCTATGCCCCACC

ACGCGACTTCGCAGCCTATCGCTCCAGGGACCAGAGGCTGCCCCCC

GATGCCCACAAGCCCCTGGGGGAGGCAGTTTCCGGACCCCCATCC

AAGAGGAGCAGGCCGACGCCCACTCCACCCTGGCCAAGATCAGAGT

GAAGTTCAGCAGGAGCGCAGACGCCCCCGCGTACCAGCAGGGCCAG

AACCAGCTCTATAACGAGCTCAATCTAGGACGAAGAGAGGAGTACG

ATGTTTTGGACAAGAGACGTGGCCGGGACCCTGAGATGGGGGAAA

GCCGAGAAGGAAGAACCCTCAGGAAGGCCTGTACAATGAACTGCAG

AAAGATAAGATGGCGGAGGCCTACAGTGAGATTGGGATGAAAGGCG

AGCGCCGGAGGGGCAAGGGGCACGATGGCCTTTACCAGGGTCTCAG

TACAGCCACCAAGGACACCTACGACGCCCTTCACATGCAGGCCCTG

CCTCCTCGCTAA
```

The nucleic acid sequence may encode the same amino acid sequence as that encoded by SEQ ID No. 15, 16, 17, 18 19 or 20 but may have a different nucleic acid sequence, due to the degeneracy of the genetic code. The nucleic acid sequence may have at least 80, 85, 90, 95, 98 or 99% identity to the sequence shown as SEQ ID No. 15, 16, 17, 18 19 or 20 provided that it encodes a CAR as defined in the first aspect of the invention.

Vector

The present invention also provides a vector which comprises a nucleic acid sequence according to the present invention. Such a vector may be used to introduce the nucleic acid sequence into a host cell so that it expresses and produces a molecule according to the first aspect of the invention.

The vector may, for example, be a plasmid or synthetic mRNA or a viral vector, such as a retroviral vector or a lentiviral vector.

The vector may be capable of transfecting or transducing an effector cell.

Host Cell

The invention also provides a host cell which comprises a nucleic acid according to the invention. The host cell may be capable of expressing a CAR according to the first aspect of the invention.

The host cell may be human T cell or a human NK cell.

A T-cell capable of expressing a CAR according to the invention may be made by transducing or transfecting a T cell with CAR-encoding nucleic acid.

The T-cell may be an ex vivo T cell. The T cell may be from a peripheral blood mononuclear cell (PBMC) sample. T cells may be activated and/or expanded prior to being transduced with CAR-encoding nucleic acid, for example by treatment with a anti-CD3 monoclonal antibody.

Pharmaceutical Composition

The present invention also relates to a pharmaceutical composition containing a vector or a CAR-expressing T cell of the invention together with a pharmaceutically acceptable carrier, diluent or excipient, and optionally one or more further pharmaceutically active polypeptides and/or compounds. Such a formulation may, for example, be in a form suitable for intravenous infusion).

Method of Treatment

T cells expressing a CAR molecule of the present invention are capable of killing cancer cells, such as multiple myeloma cells. CAR-expressing T cells may either be created ex vivo either from a patient's own peripheral blood ($1^{st}$ party), or in the setting of a haematopoietic stem cell transplant from donor peripheral blood ($2^{nd}$ party), or peripheral blood from an unconnected donor ($3^{rd}$ party). Alternatively, CAR T-cells may be derived from ex-vivo differentiation of inducible progenitor cells or embryonic progenitor cells to T-cells. In these instances, CAR T-cells are generated by introducing DNA or RNA coding for the CAR by one of many means including transduction with a viral vector, transfection with DNA or RNA.

T cells expressing a CAR molecule of the present invention may be used for the treatment of a cancerous disease, in particular a plasma cell disorder or a B cell disorder which correlates with enhanced BCMA expression.

Plasma cell disorders include plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma (POEMS Syndrome) and heavy chain diseases as well as the clinically unclear monoclonal gammopathy of undetermined significance/smoldering multiple myeloma.

The disease may be multiple myeloma.

Examples for B cell disorders which correlate with elevated BCMA expression levels are CLL (chronic lymphocytic leukemia) and non-Hodgkins lymphoma (NHL). The bispecific binding agents of the invention may also be used in the therapy of autoimmune diseases like Systemic Lupus Erythematosus (SLE), multiple sclerosis (MS) and rheumatoid arthritis (RA).

The method of the present invention may be for treating a cancerous disease, in particular a plasma cell disorder or a B cell disorder which correlates with enhanced BCMA expression.

A method for the treatment of disease relates to the therapeutic use of a vector or T cell of the invention. In this respect, the vector or T cell may be administered to a subject having an existing disease or condition in order to lessen, reduce or improve at least one symptom associated with the disease and/or to slow down, reduce or block the progression of the disease. The method of the invention may cause or promote T-cell mediated killing of BCMA-expressing cells, such as plasma cells.

The invention will now be further described by way of Examples, which are meant to serve to assist one of ordinary skill in the art in carrying out the invention and are not intended in any way to limit the scope of the invention.

EXAMPLES

Example 1—Characterisation of BCMA as a Target for Myeloma

Primary myeloma cells were isolated by performing a CD138 immunomagnetic selection on fresh bone marrow samples from Multiple myeloma patients that were known to have frank disease. These cells were stained with the BCMA specific J6MO mAb (GSK) which was conjugated to PE. At the same time, a standard of beads with known numbers of binding sites was generated using the PE Quantibrite bead kit (Becton Dickenson) as per the manufacturer's instructions. The BCMA copy number on myeloma cells could be derived by correlating the mean-fluorescent intensity from the myeloma cells with the standard curve derived from the beads. It was found that the range of BCMA copy number on a myeloma cell surface is low: at 348.7-4268.4 BCMA copies per cell with a mean of 1181 and a median of 1084.9

(FIG. 2). This is considerably lower than e.g. CD19 and GD2, classic targets for CARs. Presence of BCMA expression on primary myeloma cells was also confirmed with the Vicky-1 antibody (Abcam Ab17323), examples of which are shown in FIG. 14.

Example 2—Design and Construction of APRIL Based CARs

APRIL in its natural form is a secreted type II protein. The use of APRIL as a BCMA binding domain for a CAR requires conversion of this type II secreted protein to a type I membrane bound protein and for this protein to be stable and to retain binding to BCMA in this form. To generate candidate molecules, the extreme amino-terminus of APRIL was deleted to remove binding to proteoglycans. Next, a signal peptide was added to direct the nascent protein to the endoplasmic reticulum and hence the cell surface. Also, because the nature of spacer used can alter the function of a CAR, three different spacer domains were tested: an APRIL based CAR was generated comprising (i) a human IgG1 spacer altered to remove Fc binding motifs; (ii) a CD8 stalk; and (iii) the IgG1 hinge alone (cartoon in FIGS. 4A-4C and amino acid sequences in FIGS. 5A-5C, and also amino acid sequences in FIG. 19 which differ from the sequences in FIGS. 5A-5C by having a different signal peptide and the V5 epitope tag). These CARs were expressed in a bicistronic retroviral vector (FIG. 6A) so that a marker protein— truncated CD34 could be co-expressed as a convenient marker gene.

Example 3—Expression and Function of APRIL Based CARs

The aim of this study was to test whether the APRIL based CARs which had been constructed were expressed on the cell surface and whether APRIL had folded to form the native protein. T-cells were transduced with these different CAR constructs and stained using a commercially available anti-APRIL mAb, along with staining for the marker gene and analysed by flow-cytometry. The results of this experiment are shown in FIG. 6B where APRIL binding is plotting against marker gene fluorescence. These data show that in this format, the APRIL based CARs are expressed on the cell surface and APRIL folds sufficiently to be recognized by an anti-APRIL mAb.

Next, it was determined whether APRIL in this format could recognize BCMA and TACI. Recombinant BCMA and TACI were generated as fusions with mouse IgG2a-Fc. These recombinant proteins were incubated with the transduced T-cells. After this, the cells were washed and stained with an anti-mouse fluorophore conjugated antibody and an antibody to detect the marker gene conjugated to a different fluorophore. The cells were analysed by flow cytometry and the results are presented in FIG. 6C. The different CARs were able to bind both BCMA and TACI. Surprisingly, the CARs were better able to bind BCMA than TACI. Also, surprisingly CARs with a CD8 stalk or IgG1 hinge spacer were better able to bind BCMA and TACI than CAR with an Fc spacer.

Example 4—APRIL Based Chimeric Antigen Receptors are Active Against BCMA Expressing Cells T-cells from normal donors were transduced with the different APRIL CARs and tested against SupT1 cells either wild-type, or engineered to express BCMA and TACI. Several different assays were used to determine function. A classical chromium release assay was performed. Here, the target cells (the SupT1 cells) were labelled with $^{51}$Cr and mixed with effectors (the transduced T-cells) at different ratio. Lysis of target cells was determined by counting $^{51}$Cr in the co-culture supernatant (FIG. 6A shows the cumulative data, example data from a single assay with different effector:target ratios is shown in FIG. 12).

In addition, supernatant from T-cells cultured 1:1 with SupT1 cells was assayed by ELISA for Interferon-gamma (FIG. 6B shows cumulative data, example data from a single assay is shown in FIG. 13). Measurement of T-cell expansion after one week of co-culture with SupT1 cells was also performed (FIG. 6C). T-cells were counted by flow-cytometry calibrated with counting beads. These experimental data show that APRIL based CARs can kill BCMA expressing targets. Further, these data show that CARs based on the CD8 stalk or IgG1 hinge performed better than the Fc-pvaa based CAR.

Example 5—APRIL Based CARs are Able to Kill Primary Myeloma Cells

The above data are encouraging since they demonstrate that it in principle, it is possible to make an APRIL based CAR. However, since most primary myeloma cells express a low number of BCMA molecules on their surface, it was investigated whether such an APRIL based CAR would cause killing of primary myeloma cells, particularly in cases with low-density expression. Three cases were selected which represented the range of BCMA expression described in FIG. 2: the first had dim expression (lower than mean); the second case had intermediate expression (approximately mean expression) and the third had bright (above mean expression). FIG. 8 shows a histogram of BCMA staining against isotype control for all three cases on the left to illustrate BCMA expression. Since when comparing APRIL based CARs with different spacers it had been determined that CARs with CD8 stalk spacer and IgG1 hinge spacer performed better than the Fc-pvaa spacered CAR, in this assay, only the CD8 stalk and hinge APRIL CARs were tested. On the left, survival of myeloma cells compared with starting numbers is shown at day 3 and day 6 after a 1:1 co-culture of myeloma cells and CAR T-cells. By day 6, >95% of the myeloma cells were eliminated, including those with dim BCMA expression. Dim BCMA expressing myeloma cells can be targeted by the APRIL CARs albeit with a slower tempo of killing than higher expressers.

Example 6—Secreted and Truncated APRIL Fused to an Fc Spacer Recognizes BCMA and TACI In order to investigate whether truncated APRIL in a CAR format (i.e. fused to a transmembrane domain and anchored to a cell membrane) could bind BCMA and TACI, a basic CAR was engineered in frame with the self-cleaving foot and mouth disease 2A peptide with truncated CD34, as a convenient marker gene. A stable SUPT1 cell line was established which expresses this construct. Secreted truncated BCMA and TACI fused to human (and other species, not shown) Ig Fc domain was also generated and recombinant protein produced. It was shown that both BCMA-Fc and TACI-Fc bind the engineered SUPT1 cell line. Only cells expressing the CD34 marker gene were found to bind BCMA-Fc and TACI-Fc (FIG. 9).

Example 7—APRIL Based Chimeric Antigen Receptors are Stably Expressed on the Surface of T-Cells The CAR spacer domain can alter sensitivity and specificity. Three versions of an APRIL-based CAR were generated with three spacer domains: (i) a human IgG1 spacer altered to remove Fc binding motifs; (ii) a CD8 stalk; and (iii) the IgG1 hinge alone (FIG. 10B). Primary human T-cells were transduced with these different CARs and stained using a commercially available anti-APRIL mAb (FIG. 11).

Example 8—APRIL Based Chimeric Antigen Receptors are Active Against Cognate Target Expressing Cells T-cells from normal donors were transduced with the different APRIL CARs and tested against SupT1 cells either wild-type, or engineered to express BCMA and TACI. Several different assays were used to determine function. A classical chromium release assay was performed. Here, the target cells (the SupT1 cells) were labelled with $^{51}$Cr and mixed with effectors (the transduced T-cells) at different ratio. Lysis of target cells was determined by counting $^{51}$Cr in the co-culture supernatant (FIG. 12).

In addition, supernatant from T-cells cultured 1:1 with SupT1 cells was assayed by ELISA for Interferon-gamma (FIG. 13).

Measurement of T-cell expansion after one week of co-culture with SupT1 cells was also performed. T-cells were counted by flow-cytometry calibrated with counting beads. Initial data (not shown) appears to indicate that the CD8 stalk based construct results in more T-cell proliferation than the other constructs.

Example 9—Demonstration of In Vivo Function of APRIL CAR T-Cells

In order to demonstrate APRIL CAR T-cell function in vivo, APRIL CAR T-cells were tested in a human/mouse chimeric model. MM1.s (ATCC CRL-2974) is a human myeloma cell line which expresses intermediate levels of BCMA. The inventors engineered this cell line to express firefly Luciferase to derive the cell-line MM1.s.FLuc.

NOD scid gamma (NSG: NOD.Cg-Prkdcsc$^{scid}$ Il2rgtm1$^{Wjl/SzJ}$) mice are profoundly immunosuppressed mice capable of engrafting several human cell lines and human peripheral blood lymphocytes. Three month old female NSG mice received 1×10$^7$ MM1.s.FLuc cells vial tail-vein injection without any preparative therapy. Engraftment was determined by serial bioluminescence imaging (FIG. 16). Robust and increasing intramedullary engraftment was observed in all mice. At day 13, 5×10$^6$ APRIL-HNG-CD28OXZ CAR T-cells were administered via tail vein injection. Serial bioluminescence was performed which showed rapid decrease in burden of MM1.s (FIG. 16) in all treated mice to a complete remission. This response to CAR therapy was confirmed by flow-cytometry and immunohistochemistry.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

---

The invention claimed is:

1. A chimeric antigen receptor (CAR) which comprises:
   (i) truncated proliferation-inducing ligand (APRIL) that
      (a) binds B cell maturation antigen (BCMA) and
      (b) binds transmembrane activator and calcium modulator and cylophilin ligand interactor (TACI);
   (ii) a spacer domain; and
   (ii) a transmembrane domain; and
   (iii) an intracellular T cell signaling domain.

2. The CAR according to claim 1, wherein the truncated APRIL lacks the amino terminal portion of APRIL responsible for proteoglycan binding.

3. The CAR according to claim 2, which comprises the sequence shown as SEQ ID No. 14.

4. The CAR according to claim 1, wherein the transmembrane and intracellular T-cell signalling domain comprise the sequence shown as SEQ ID No. 7.

5. The A CAR according to claim 1, wherein the spacer comprises one of the following: a human IgG1 spacer; an IgG1 hinge; or a CD8 stalk.

6. The CAR according to claim 5, wherein the spacer comprises a CD8 stalk.

7. The CAR according to claim 1, which comprises the sequence shown as SEQ ID No. 1, 2, 3, 4, 5 or 6.

* * * * *

UNITED STATES PATENT AND TRADEMARK OFFICE
CERTIFICATE OF CORRECTION

PATENT NO. : 10,919,951 B2  
APPLICATION NO. : 16/162747  
DATED : February 16, 2021  
INVENTOR(S) : Pule et al.

Page 1 of 1

It is certified that error appears in the above-identified patent and that said Letters Patent is hereby corrected as shown below:

On the Title Page

Item (57), Line 2, "comprising;" should be -- comprising: --.

Item (57), Line 4, "domain" should be -- domain; --.

In the Claims

At Column 53, Line 51, "domain; and" should be -- domain; --.

At Column 53, Line 52, "(ii)" should be -- (iii) --.

At Column 53, Line 53, "(iii)" should be -- (iv) --.

At Column 54, Line 50, "The A" should be -- The --.

Signed and Sealed this  
Second Day of November, 2021

Drew Hirshfeld  
*Performing the Functions and Duties of the  
Under Secretary of Commerce for Intellectual Property and  
Director of the United States Patent and Trademark Office*

SEQUENCE LISTING

```
<160> NUMBER OF SEQ ID NOS: 21

<210> SEQ ID NO 1
<211> LENGTH: 614
<212> TYPE: PRT
<213> ORGANISM: Artificial Sequence
<220> FEATURE:
<223> OTHER INFORMATION: Chimeric antigen receptor (CAR)
      dAPRIL-HCH2CH3pvaa-CD28OXZ

<400> SEQUENCE: 1

Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
                20                  25                  30

Lys Asp Asp Ser Asp Val Thr Glu Val Met Trp Gln Pro Ala Leu Arg
            35                  40                  45

Arg Gly Arg Gly Leu Gln Ala Gln Gly Tyr Gly Val Arg Ile Gln Asp
        50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
                100                 105                 110
```

```
Tyr Asn Ser Cys Tyr Ser Ala Gly Val Phe His Leu His Gln Gly Asp
            115                 120                 125

Ile Leu Ser Val Ile Ile Pro Arg Ala Arg Ala Lys Leu Asn Leu Ser
        130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Ala Pro Pro Val Ala Gly Pro Ser Val Phe Leu Phe Pro Pro
            180                 185                 190

Lys Pro Lys Asp Thr Leu Met Ile Ala Arg Thr Pro Glu Val Thr Cys
        195                 200                 205

Val Val Val Asp Val Ser His Glu Asp Pro Glu Val Lys Phe Asn Trp
210                 215                 220

Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
        275                 280                 285

Gln Pro Arg Glu Pro Gln Val Tyr Thr Leu Pro Pro Ser Arg Asp Glu
290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
            340                 345                 350

Leu Tyr Ser Lys Leu Thr Val Asp Lys Ser Arg Trp Gln Gln Gly Asn
        355                 360                 365

Val Phe Ser Cys Ser Val Met His Glu Ala Leu His Asn His Tyr Thr
370                 375                 380

Gln Lys Ser Leu Ser Leu Ser Pro Gly Lys Lys Asp Pro Lys Phe Trp
385                 390                 395                 400

Val Leu Val Val Val Gly Gly Val Leu Ala Cys Tyr Ser Leu Leu Val
                405                 410                 415

Thr Val Ala Phe Ile Ile Phe Trp Val Arg Ser Lys Arg Ser Arg Leu
            420                 425                 430

Leu His Ser Asp Tyr Met Asn Met Thr Pro Arg Arg Pro Gly Pro Thr
        435                 440                 445

Arg Lys His Tyr Gln Pro Tyr Ala Pro Pro Arg Asp Phe Ala Ala Tyr
450                 455                 460

Arg Ser Arg Asp Gln Arg Leu Pro Pro Asp Ala His Lys Pro Pro Gly
465                 470                 475                 480

Gly Gly Ser Phe Arg Thr Pro Ile Gln Glu Glu Gln Ala Asp Ala His
                485                 490                 495

Ser Thr Leu Ala Lys Ile Arg Val Lys Phe Ser Arg Ser Ala Asp Ala
            500                 505                 510

Pro Ala Tyr Gln Gln Gly Gln Asn Gln Leu Tyr Asn Glu Leu Asn Leu
        515                 520                 525
```

```
Gly Arg Arg Glu Glu Tyr Asp Val Leu Asp Lys Arg Gly Arg Asp
            530                 535                 540

Pro Glu Met Gly Gly Lys Pro Arg Arg Lys Asn Pro Gln Glu Gly Leu
545                 550                 555                 560

Tyr Asn Glu Leu Gln Lys Asp Lys Met Ala Glu Ala Tyr Ser Glu Ile
                565                 570                 575

Gly Met Lys Gly Glu Arg Arg Arg Gly Lys Gly His Asp Gly Leu Tyr
                580                 585                 590

Gln Gly Leu Ser Thr Ala Thr Lys Asp Thr Tyr Asp Ala Leu His Met
            595                 600                 605

Gln Ala Leu Pro Pro Arg
            610
```

<210> SEQ ID NO 2
<211> LENGTH: 424
<212> TYPE: PRT
<213> ORGANISM: Artificial Sequence
<220> FEATURE:
<223> OTHER INFORMATION: Chimeric antigen receptor (CAR)
      dAPRIL-CD8STK-CD28OXZ

<400> SEQUENCE: 2

```
Met Glu Thr Asp Thr Leu Leu Leu Trp Val Leu Leu Leu Trp Val Pro
1               5                   10                  15

Gly Ser Thr Gly Ser Val Leu His Leu Val Pro Ile Asn Ala Thr Ser
                20                  25                  30

Lys Asp Asp Ser Asp Val Thr Glu Val Met Trp Gln Pro Ala Leu Arg
            35                  40                  45

Arg Gly Arg Gly Leu Gln Ala Gln Gly Tyr Gly Val Arg Ile Gln Asp
        50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Thr Thr Thr Pro Ala Pro Arg Pro Pro Thr Pro Ala Pro Thr
                165                 170                 175

Ile Ala Ser Gln Pro Leu Ser Leu Arg Pro Glu Ala Cys Arg Pro Ala
            180                 185                 190

Ala Gly Gly Ala Val His Thr Arg Gly Leu Asp Phe Ala Cys Asp Ile
        195                 200                 205

Phe Trp Val Leu Val Val Val Gly Gly Val Leu Ala Cys Tyr Ser Leu
    210                 215                 220

Leu Val Thr Val Ala Phe Ile Ile Phe Trp Val Arg Ser Lys Arg Ser
225                 230                 235                 240

Arg Leu Leu His Ser Asp Tyr Met Asn Met Thr Pro Arg Arg Pro Gly
                245                 250                 255

Pro Thr Arg Lys His Tyr Gln Pro Tyr Ala Pro Pro Arg Asp Phe Ala
            260                 265                 270
```

```
Ala Tyr Arg Ser Arg Asp Gln Arg Leu Pro Pro Asp Ala His Lys Pro
            275                 280                 285

Pro Gly Gly Gly Ser Phe Arg Thr Pro Ile Gln Glu Gln Ala Asp
290                 295                 300

Ala His Ser Thr Leu Ala Lys Ile Arg Val Lys Phe Ser Arg Ser Ala
305                 310                 315                 320

Asp Ala Pro Ala Tyr Gln Gln Gly Gln Asn Gln Leu Tyr Asn Glu Leu
                325                 330                 335

Asn Leu Gly Arg Arg Glu Glu Tyr Asp Val Leu Asp Lys Arg Arg Gly
            340                 345                 350

Arg Asp Pro Glu Met Gly Gly Lys Pro Arg Arg Lys Asn Pro Gln Glu
        355                 360                 365

Gly Leu Tyr Asn Glu Leu Gln Lys Asp Lys Met Ala Glu Ala Tyr Ser
    370                 375                 380

Glu Ile Gly Met Lys Gly Glu Arg Arg Arg Gly Lys Gly His Asp Gly
385                 390                 395                 400

Leu Tyr Gln Gly Leu Ser Thr Ala Thr Lys Asp Thr Tyr Asp Ala Leu
                405                 410                 415

His Met Gln Ala Leu Pro Pro Arg
            420

<210> SEQ ID NO 3
<211> LENGTH: 398
<212> TYPE: PRT
<213> ORGANISM: Artificial Sequence
<220> FEATURE:
<223> OTHER INFORMATION: Chimeric antigen receptor (CAR)
      dAPRIL-HNG-CD28OXZ

<400> SEQUENCE: 3

Met Glu Thr Asp Thr Leu Leu Leu Trp Val Leu Leu Trp Val Pro
1               5                   10                  15

Gly Ser Thr Gly Ser Val Leu His Leu Val Pro Ile Asn Ala Thr Ser
                20                  25                  30

Lys Asp Asp Ser Asp Val Thr Glu Val Met Trp Gln Pro Ala Leu Arg
            35                  40                  45

Arg Gly Arg Gly Leu Gln Ala Gln Gly Tyr Gly Val Arg Ile Gln Asp
        50                  55                  60

Ala Gly Val Tyr Leu Leu Tyr Ser Gln Val Leu Phe Gln Asp Val Thr
65                  70                  75                  80

Phe Thr Met Gly Gln Val Val Ser Arg Glu Gly Gln Gly Arg Gln Glu
                85                  90                  95

Thr Leu Phe Arg Cys Ile Arg Ser Met Pro Ser His Pro Asp Arg Ala
            100                 105                 110

Tyr Asn Ser Cys Tyr Ser Ala Gly Val Phe His Leu His Gln Gly Asp
        115                 120                 125

Ile Leu Ser Val Ile Ile Pro Arg Ala Arg Ala Lys Leu Asn Leu Ser
    130                 135                 140

Pro His Gly Thr Phe Leu Gly Phe Val Lys Leu Ser Gly Gly Gly Ser
145                 150                 155                 160

Asp Pro Ala Glu Pro Lys Ser Pro Asp Lys Thr His Thr Cys Pro Pro
                165                 170                 175

Cys Pro Lys Asp Pro Lys Phe Trp Val Leu Val Val Val Gly Gly Val
            180                 185                 190

Leu Ala Cys Tyr Ser Leu Leu Val Thr Val Ala Phe Ile Ile Phe Trp
```

-continued

```
                195                 200                 205
Val Arg Ser Lys Arg Ser Arg Leu Leu His Ser Asp Tyr Met Asn Met
210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser Arg Asp Gln Arg Leu Pro
                245                 250                 255

Pro Asp Ala His Lys Pro Pro Gly Gly Gly Ser Phe Arg Thr Pro Ile
                260                 265                 270

Gln Glu Glu Gln Ala Asp Ala His Ser Thr Leu Ala Lys Ile Arg Val
            275                 280                 285

Lys Phe Ser Arg Ser Ala Asp Ala Pro Ala Tyr Gln Gln Gly Gln Asn
            290                 295                 300

Gln Leu Tyr Asn Glu Leu Asn Leu Gly Arg Arg Glu Glu Tyr Asp Val
305                 310                 315                 320

Leu Asp Lys Arg Arg Gly Arg Asp Pro Glu Met Gly Gly Lys Pro Arg
                325                 330                 335

Arg Lys Asn Pro Gln Glu Gly Leu Tyr Asn Glu Leu Gln Lys Asp Lys
                340                 345                 350

Met Ala Glu Ala Tyr Ser Glu Ile Gly Met Lys Gly Glu Arg Arg Arg
            355                 360                 365

Gly Lys Gly His Asp Gly Leu Tyr Gln Gly Leu Ser Thr Ala Thr Lys
370                 375                 380

Asp Thr Tyr Asp Ala Leu His Met Gln Ala Leu Pro Pro Arg
385                 390                 395
```

<210> SEQ ID NO 4
<211> LENGTH: 633
<212> TYPE: PRT
<213> ORGANISM: Artificial Sequence
<220> FEATURE:
<223> OTHER INFORMATION: Chimeric antigen receptor (CAR)
    dAPRIL-HCH2CH3pvaa-CD28OXZ

<400> SEQUENCE: 4

```
Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
                20                  25                  30

Ser Thr Ser Gly Gly Gly Gly Ser Val Leu His Leu Val Pro Ile Asn
            35                  40                  45

Ala Thr Ser Lys Asp Asp Ser Asp Val Thr Glu Val Met Trp Gln Pro
50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
                100                 105                 110

Arg Gln Glu Thr Leu Phe Arg Cys Ile Arg Ser Met Pro Ser His Pro
            115                 120                 125

Asp Arg Ala Tyr Asn Ser Cys Tyr Ser Ala Gly Val Phe His Leu His
            130                 135                 140

Gln Gly Asp Ile Leu Ser Val Ile Ile Pro Arg Ala Arg Ala Lys Leu
145                 150                 155                 160
```

```
Asn Leu Ser Pro His Gly Thr Phe Leu Gly Phe Val Lys Leu Ser Gly
                165                 170                 175
Gly Gly Ser Asp Pro Ala Glu Pro Lys Ser Pro Asp Lys Thr His Thr
            180                 185                 190
Cys Pro Pro Cys Pro Ala Pro Pro Val Ala Gly Pro Ser Val Phe Leu
            195                 200                 205
Phe Pro Pro Lys Pro Lys Asp Thr Leu Met Ile Ala Arg Thr Pro Glu
    210                 215                 220
Val Thr Cys Val Val Val Asp Val Ser His Glu Asp Pro Glu Val Lys
225                 230                 235                 240
Phe Asn Trp Tyr Val Asp Gly Val Glu Val His Asn Ala Lys Thr Lys
                245                 250                 255
Pro Arg Glu Glu Gln Tyr Asn Ser Thr Tyr Arg Val Val Ser Val Leu
            260                 265                 270
Thr Val Leu His Gln Asp Trp Leu Asn Gly Lys Glu Tyr Lys Cys Lys
        275                 280                 285
Val Ser Asn Lys Ala Leu Pro Ala Pro Ile Glu Lys Thr Ile Ser Lys
    290                 295                 300
Ala Lys Gly Gln Pro Arg Glu Pro Gln Val Tyr Thr Leu Pro Pro Ser
305                 310                 315                 320
Arg Asp Glu Leu Thr Lys Asn Gln Val Ser Leu Thr Cys Leu Val Lys
                325                 330                 335
Gly Phe Tyr Pro Ser Asp Ile Ala Val Glu Trp Glu Ser Asn Gly Gln
            340                 345                 350
Pro Glu Asn Asn Tyr Lys Thr Thr Pro Pro Val Leu Asp Ser Asp Gly
        355                 360                 365
Ser Phe Phe Leu Tyr Ser Lys Leu Thr Val Asp Lys Ser Arg Trp Gln
    370                 375                 380
Gln Gly Asn Val Phe Ser Cys Ser Val Met His Glu Ala Leu His Asn
385                 390                 395                 400
His Tyr Thr Gln Lys Ser Leu Ser Leu Ser Pro Gly Lys Lys Asp Pro
                405                 410                 415
Lys Phe Trp Val Leu Val Val Val Gly Gly Val Leu Ala Cys Tyr Ser
            420                 425                 430
Leu Leu Val Thr Val Ala Phe Ile Ile Phe Trp Val Arg Ser Lys Arg
        435                 440                 445
Ser Arg Leu Leu His Ser Asp Tyr Met Asn Met Thr Pro Arg Arg Pro
    450                 455                 460
Gly Pro Thr Arg Lys His Tyr Gln Pro Tyr Ala Pro Pro Arg Asp Phe
465                 470                 475                 480
Ala Ala Tyr Arg Ser Arg Asp Gln Arg Leu Pro Pro Asp Ala His Lys
                485                 490                 495
Pro Pro Gly Gly Gly Ser Phe Arg Thr Pro Ile Gln Glu Glu Gln Ala
            500                 505                 510
Asp Ala His Ser Thr Leu Ala Lys Ile Arg Val Lys Phe Ser Arg Ser
        515                 520                 525
Ala Asp Ala Pro Ala Tyr Gln Gln Gly Gln Asn Gln Leu Tyr Asn Glu
    530                 535                 540
Leu Asn Leu Gly Arg Arg Glu Glu Tyr Asp Val Leu Asp Lys Arg Arg
545                 550                 555                 560
Gly Arg Asp Pro Glu Met Gly Gly Lys Pro Arg Arg Lys Asn Pro Gln
                565                 570                 575
Glu Gly Leu Tyr Asn Glu Leu Gln Lys Asp Lys Met Ala Glu Ala Tyr
```

```
                    580                 585                 590
Ser Glu Ile Gly Met Lys Gly Glu Arg Arg Gly Lys Gly His Asp
                595                 600                 605

Gly Leu Tyr Gln Gly Leu Ser Thr Ala Thr Lys Asp Thr Tyr Asp Ala
            610                 615                 620

Leu His Met Gln Ala Leu Pro Pro Arg
625                 630

<210> SEQ ID NO 5
<211> LENGTH: 443
<212> TYPE: PRT
<213> ORGANISM: Artificial Sequence
<220> FEATURE:
<223> OTHER INFORMATION: Chimeric antigen receptor (CAR)
      dAPRIL-CD8STK-CD28OXZ

<400> SEQUENCE: 5

Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
            20                  25                  30

Ser Thr Ser Gly Gly Gly Gly Ser Val Leu His Leu Val Pro Ile Asn
        35                  40                  45

Ala Thr Ser Lys Asp Asp Ser Asp Val Thr Glu Val Met Trp Gln Pro
    50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
            100                 105                 110

Arg Gln Glu Thr Leu Phe Arg Cys Ile Arg Ser Met Pro Ser His Pro
        115                 120                 125

Asp Arg Ala Tyr Asn Ser Cys Tyr Ser Ala Gly Val Phe His Leu His
    130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Thr Thr Thr Pro Ala Pro Arg Pro Pro Thr Pro
            180                 185                 190

Ala Pro Thr Ile Ala Ser Gln Pro Leu Ser Leu Arg Pro Glu Ala Cys
        195                 200                 205

Arg Pro Ala Ala Gly Gly Ala Val His Thr Arg Gly Leu Asp Phe Ala
    210                 215                 220

Cys Asp Ile Phe Trp Val Leu Val Val Gly Gly Val Leu Ala Cys
225                 230                 235                 240

Tyr Ser Leu Leu Val Thr Val Ala Phe Ile Ile Phe Trp Val Arg Ser
                245                 250                 255

Lys Arg Ser Arg Leu Leu His Ser Asp Tyr Met Asn Met Thr Pro Arg
            260                 265                 270

Arg Pro Gly Pro Thr Arg Lys His Tyr Gln Pro Tyr Ala Pro Pro Arg
        275                 280                 285

Asp Phe Ala Ala Tyr Arg Ser Arg Asp Gln Arg Leu Pro Pro Asp Ala
    290                 295                 300
```

-continued

His Lys Pro Pro Gly Gly Ser Phe Arg Thr Pro Ile Gln Glu Glu
305                 310                 315                 320

Gln Ala Asp Ala His Ser Thr Leu Ala Lys Ile Arg Val Lys Phe Ser
            325                 330                 335

Arg Ser Ala Asp Ala Pro Ala Tyr Gln Gln Gly Gln Asn Gln Leu Tyr
            340                 345                 350

Asn Glu Leu Asn Leu Gly Arg Arg Glu Glu Tyr Asp Val Leu Asp Lys
        355                 360                 365

Arg Arg Gly Arg Asp Pro Glu Met Gly Gly Lys Pro Arg Arg Lys Asn
370                 375                 380

Pro Gln Glu Gly Leu Tyr Asn Glu Leu Gln Lys Asp Lys Met Ala Glu
385                 390                 395                 400

Ala Tyr Ser Glu Ile Gly Met Lys Gly Glu Arg Arg Arg Gly Lys Gly
                405                 410                 415

His Asp Gly Leu Tyr Gln Gly Leu Ser Thr Ala Thr Lys Asp Thr Tyr
            420                 425                 430

Asp Ala Leu His Met Gln Ala Leu Pro Pro Arg
            435                 440

<210> SEQ ID NO 6
<211> LENGTH: 417
<212> TYPE: PRT
<213> ORGANISM: Artificial Sequence
<220> FEATURE:
<223> OTHER INFORMATION: Chimeric antigen receptor (CAR)
      dAPRIL-HNG-CD28OXZ

<400> SEQUENCE: 6

Met Gly Thr Ser Leu Leu Cys Trp Met Ala Leu Cys Leu Leu Gly Ala
1               5                   10                  15

Asp His Ala Asp Gly Lys Pro Ile Pro Asn Pro Leu Leu Gly Leu Asp
            20                  25                  30

Ser Thr Ser Gly Gly Gly Gly Ser Val Leu His Leu Val Pro Ile Asn
        35                  40                  45

Ala Thr Ser Lys Asp Asp Ser Asp Val Thr Glu Val Met Trp Gln Pro
50                  55                  60

Ala Leu Arg Arg Gly Arg Gly Leu Gln Ala Gln Gly Tyr Gly Val Arg
65                  70                  75                  80

Ile Gln Asp Ala Gly Val Tyr Leu Leu Tyr Ser Gln Val Leu Phe Gln
                85                  90                  95

Asp Val Thr Phe Thr Met Gly Gln Val Val Ser Arg Glu Gly Gln Gly
            100                 105                 110

Arg Gln Glu Thr Leu Phe Arg Cys Ile Arg Ser Met Pro Ser His Pro
        115                 120                 125

Asp Arg Ala Tyr Asn Ser Cys Tyr Ser Ala Gly Val Phe His Leu His
130                 135                 140

Gln Gly Asp Ile Leu Ser Val Ile Ile Pro Arg Ala Arg Ala Lys Leu
145                 150                 155                 160

Asn Leu Ser Pro His Gly Thr Phe Leu Gly Phe Val Lys Leu Ser Gly
                165                 170                 175

Gly Gly Ser Asp Pro Ala Glu Pro Lys Ser Pro Asp Lys Thr His Thr
            180                 185                 190

Cys Pro Pro Cys Pro Lys Asp Pro Lys Phe Trp Val Leu Val Val Val
        195                 200                 205

Gly Gly Val Leu Ala Cys Tyr Ser Leu Leu Val Thr Val Ala Phe Ile
210                 215                 220

Ile Phe Trp Val Arg Ser Lys Arg Ser Arg Leu Leu His Ser Asp Tyr
225                 230                 235                 240

Met Asn Met Thr Pro Arg Arg Pro Gly Pro Thr Arg Lys His Tyr Gln
            245                 250                 255

Pro Tyr Ala Pro Pro Arg Asp Phe Ala Ala Tyr Arg Ser Arg Asp Gln
        260                 265                 270

Arg Leu Pro Pro Asp Ala His Lys Pro Pro Gly Gly Gly Ser Phe Arg
        275                 280                 285

Thr Pro Ile Gln Glu Glu Gln Ala Asp Ala His Ser Thr Leu Ala Lys
        290                 295                 300

Ile Arg Val Lys Phe Ser Arg Ser Ala Asp Ala Pro Ala Tyr Gln Gln
305                 310                 315                 320

Gly Gln Asn Gln Leu Tyr Asn Glu Leu Asn Leu Gly Arg Arg Glu Glu
                325                 330                 335

Tyr Asp Val Leu Asp Lys Arg Gly Arg Asp Pro Glu Met Gly Gly
        340                 345                 350

Lys Pro Arg Arg Lys Asn Pro Gln Glu Gly Leu Tyr Asn Glu Leu Gln
        355                 360                 365

Lys Asp Lys Met Ala Glu Ala Tyr Ser Glu Ile Gly Met Lys Gly Glu
370                 375                 380

Arg Arg Arg Gly Lys Gly His Asp Gly Leu Tyr Gln Gly Leu Ser Thr
385                 390                 395                 400

Ala Thr Lys Asp Thr Tyr Asp Ala Leu His Met Gln Ala Leu Pro Pro
                405                 410                 415

Arg

<210> SEQ ID NO 7
<211> LENGTH: 216
<212> TYPE: PRT
<213> ORGANISM: Artificial Sequence
<220> FEATURE:
<223> OTHER INFORMATION: Transmembrane and intracellular T-cell
      signalling domain (endodomain)

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser Arg Asp Gln Arg Leu Pro Pro Asp Ala His Lys Pro
65                  70                  75                  80

Pro Gly Gly Gly Ser Phe Arg Thr Pro Ile Gln Glu Glu Gln Ala Asp
                85                  90                  95

Ala His Ser Thr Leu Ala Lys Ile Arg Val Lys Phe Ser Arg Ser Ala
            100                 105                 110

Asp Ala Pro Ala Tyr Gln Gln Gly Gln Asn Gln Leu Tyr Asn Glu Leu
        115                 120                 125

Asn Leu Gly Arg Arg Glu Glu Tyr Asp Val Leu Asp Lys Arg Arg Gly
    130                 135                 140

Arg Asp Pro Glu Met Gly Gly Lys Pro Arg Arg Lys Asn Pro Gln Glu
145                 150                 155                 160

Gly Leu Tyr Asn Glu Leu Gln Lys Asp Lys Met Ala Glu Ala Tyr Ser
            165                 170                 175

Glu Ile Gly Met Lys Gly Glu Arg Arg Gly Lys Gly His Asp Gly
        180                 185                 190

Leu Tyr Gln Gly Leu Ser Thr Ala Thr Lys Asp Thr Tyr Asp Ala Leu
            195                 200                 205

His Met Gln Ala Leu Pro Pro Arg
    210                 215

<210> SEQ ID NO 8
<211> LENGTH: 21
<212> TYPE: PRT
<213> ORGANISM: Artificial Sequence
<220> FEATURE:
<223> OTHER INFORMATION: Signal peptide

<400> SEQUENCE: 8

Met Gly Thr Ser Leu Leu Cys Trp Met Ala Leu Cys Leu Leu Gly Ala
1               5                   10                  15

Asp His Ala Asp Gly
            20

<210> SEQ ID NO 9
<211> LENGTH: 20
<212> TYPE: PRT
<213> ORGANISM: Artificial Sequence
<220> FEATURE:
<223> OTHER INFORMATION: Signal peptide

<400> SEQUENCE: 9

Met Glu Thr Asp Thr Leu Leu Leu Trp Val Leu Leu Leu Trp Val Pro
1               5                   10                  15

Gly Ser Thr Gly
            20

<210> SEQ ID NO 10
<211> LENGTH: 234
<212> TYPE: PRT
<213> ORGANISM: Artificial Sequence
<220> FEATURE:
<223> OTHER INFORMATION: Spacer (hinge-CH2CH3 of human IgG1)

<400> SEQUENCE: 10

Ala Glu Pro Lys Ser Pro Asp Lys Thr His Thr Cys Pro Pro Cys Pro
1               5                   10                  15

Ala Pro Pro Val Ala Gly Pro Ser Val Phe Leu Phe Pro Pro Lys Pro
            20                  25                  30

Lys Asp Thr Leu Met Ile Ala Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

```
Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Lys Asp
225                 230

<210> SEQ ID NO 11
<211> LENGTH: 46
<212> TYPE: PRT
<213> ORGANISM: Artificial Sequence
<220> FEATURE:
<223> OTHER INFORMATION: Spacer (human CD8 stalk)

<400> SEQUENCE: 11

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile
            35                  40                  45

<210> SEQ ID NO 12
<211> LENGTH: 20
<212> TYPE: PRT
<213> ORGANISM: Artificial Sequence
<220> FEATURE:
<223> OTHER INFORMATION: Spacer (human IgG1 hinge)

<400> SEQUENCE: 12

Ala Glu Pro Lys Ser Pro Asp Lys Thr His Thr Cys Pro Pro Cys Pro
1               5                   10                  15

Lys Asp Pro Lys
            20

<210> SEQ ID NO 13
<211> LENGTH: 250
<212> TYPE: PRT
<213> ORGANISM: Homo sapiens

<400> SEQUENCE: 13

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
            35                  40                  45

Leu Thr Gln Gln Thr Glu Leu Gln Ser Leu Arg Arg Glu Val Ser Arg
        50                  55                  60

Leu Gln Gly Thr Gly Gly Pro Ser Gln Asn Gly Glu Gly Tyr Pro Trp
65                  70                  75                  80
```

Gln Ser Leu Pro Glu Gln Ser Asp Ala Leu Glu Ala Trp Glu Asn
            85                  90                  95

Gly Glu Arg Ser Arg Lys Arg Ala Val Leu Thr Gln Lys Gln Lys
        100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
        210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 14
<211> LENGTH: 134
<212> TYPE: PRT
<213> ORGANISM: Homo sapiens

<400> SEQUENCE: 14

Val Leu His Leu Val Pro Ile Asn Ala Thr Ser Lys Asp Asp Ser Asp
1               5                   10                  15

Val Thr Glu Val Met Trp Gln Pro Ala Leu Arg Arg Gly Arg Gly Leu
            20                  25                  30

Gln Ala Gln Gly Tyr Gly Val Arg Ile Gln Asp Ala Gly Val Tyr Leu
        35                  40                  45

Leu Tyr Ser Gln Val Leu Phe Gln Asp Val Thr Phe Thr Met Gly Gln
    50                  55                  60

Val Val Ser Arg Glu Gly Gln Gly Arg Gln Glu Thr Leu Phe Arg Cys
65                  70                  75                  80

Ile Arg Ser Met Pro Ser His Pro Asp Arg Ala Tyr Asn Ser Cys Tyr
                85                  90                  95

Ser Ala Gly Val Phe His Leu His Gln Gly Asp Ile Leu Ser Val Ile
            100                 105                 110

Ile Pro Arg Ala Arg Ala Lys Leu Asn Leu Ser Pro His Gly Thr Phe
        115                 120                 125

Leu Gly Phe Val Lys Leu
    130

<210> SEQ ID NO 15
<211> LENGTH: 1845
<212> TYPE: DNA
<213> ORGANISM: Artificial Sequence
<220> FEATURE:
<223> OTHER INFORMATION: Nucleic acid sequences coding for a CAR
      (dAPRIL-HCH2CH3pvaa-CD28OXZ)

<400> SEQUENCE: 15

```
atggagaccg acaccctgct gctgtgggtg ctgctgctgt gggtgccagg cagcaccggc    60
agcgtgctcc acctggtgcc catcaacgcc accagcaagg acgactctga tgtgaccgag   120
gtgatgtggc agccagccct gagacggggc agaggcctgc aggcccaggg ctacggcgtg   180
agaatccagg acgctggcgt gtacctgctg tactcccagg tgctgttcca ggacgtgacc   240
ttcacaatgg gccaggtggt gagccgggag ggccagggca gacaggagac cctgttccgg   300
tgcatccgga gcatgcccag ccaccccgac agagcctaca acagctgcta cagcgctggc   360
gtgtttcacc tgcaccaggg cgacatcctg agcgtgatca tccccagagc cagagccaag   420
ctgaacctgt ccccccacgg cacctttctg gcttcgtga gctgtctgg aggcggctcg   480 gatcccgccg agcccaaatc tcctgacaaa actcacacat gcccaccgtg cccagcacct   540
cccgtggccg gccgtcagt cttcctcttc cccccaaaac ccaaggacac cctcatgatc   600
gcccggaccc ctgaggtcac atgcgtggtg gtggacgtga gccacgaaga ccctgaggtc   660
aagttcaact ggtacgtgga cggcgtggag gtgcataatg ccaagacaaa gccgcgggag   720
gagcagtaca acagcacgta ccgtgtggtc agcgtcctca ccgtcctgca ccaggactgg   780
ctgaatggca aggagtacaa gtgcaaggtc tccaacaaag ccctcccagc ccccatcgag   840
aaaaccatct ccaaagccaa agggcagccc cgagaaccac aggtgtacac cctgccccca   900
tcccgggatg agctgaccaa gaaccaggtc agcctgacct gcctggtcaa aggcttctat   960
cccagcgaca tcgccgtgga gtgggagagc aatgggcaac cggagaacaa ctacaagacc  1020
acgcctcccg tgctggactc cgacggctcc ttcttcctct acagcaagct caccgtggac  1080
aagagcaggt ggcagcaggg gaacgtcttc tcatgctccg tgatgcatga ggctctgcac  1140
aaccactaca cgcagaagag cctctccctg tctccgggta aaaaagatcc caaattttgg  1200
gtgctggtgg tggttggtgg agtcctggct tgctatagct tgctagtaac agtggccttt  1260
attattttct gggtgaggag taagaggagc aggctcctgc acagtgacta catgaacatg  1320
actccccgcc gccccgggcc cacccgcaag cattaccagc cctatgcccc accacgcgac  1380
ttcgcagcct atcgctccag ggaccagagg ctgccccccg atgccacaa gcccctgggc  1440 ggaggcagtt tccggacccc catccaagag gagcaggccg acgcccactc caccctggcc  1500
aagatcagag tgaagttcag caggagcgca gacgccccccg cgtaccagca gggccagaac  1560
cagctctata cgagctcaa tctaggacga gagaggagt cgatgttttt ggacaagaga  1620
cgtggccggg accctgagat ggggggaaag ccgagaagga agaaccctca ggaaggcctg  1680
tacaatgaac tgcagaaaga taagatgcg gaggcctaca gtgagattgg gatgaaaggc  1740
gagcgccgga ggggcaaggg gcacgatggc ctttaccagg gtctcagtac agccaccaag  1800
gacacctacg acgcccttca catgcaggcc ctgcctcctc gctaa                  1845
```

<210> SEQ ID NO 16
<211> LENGTH: 1275
<212> TYPE: DNA
<213> ORGANISM: Artificial Sequence
<220> FEATURE:
<223> OTHER INFORMATION: Nucleic acid sequences coding for a CAR
      (dAPRIL-CD8STK-CD28OXZ)

<400> SEQUENCE: 16

```
atggagaccg acaccctgct gctgtgggtg ctgctgctgt gggtgccagg cagcaccggc    60
agcgtgctcc acctggtgcc catcaacgcc accagcaagg acgactctga tgtgaccgag   120
gtgatgtggc agccagccct gagacggggc agaggcctgc aggcccaggg ctacggcgtg   180
```

```
agaatccagg acgctggcgt gtacctgctg tactcccagg tgctgttcca ggacgtgacc    240
ttcacaatgg gccaggtggt gagccgggag ggccagggca gacaggagac cctgttccgg    300
tgcatccgga gcatgcccag ccaccccgac agagcctaca cagctgcta cagcgctggc     360 gtgtttcacc tgcaccaggg cgacatcctg agcgtgatca tccccagagc cagagccaag    420
ctgaacctgt ccccccacgg caccttctg ggcttcgtga agctgtctgg aggcggctcg     480
gatcccacca cgacgccagc gccgcgacca ccaacaccgg cgcccaccat cgcgtcgcag    540
ccccctgtcc ctgcgcccga ggcgtgccgg ccagcggcgg ggggcgcagt gcacacgagg    600
gggctggact tcgcctgtga tatcttttgg gtgctggtgg tggttggtgg agtcctggct    660
tgctatagct tgctagtaac agtggccttt attattttct gggtgaggag taagaggagc    720
aggctcctgc acagtgacta catgaacatg actccccgcc gccccgggcc cacccgcaag    780
cattaccagc cctatgcccc accacgcgac ttcgcagcct atcgctccag ggaccagagg    840
ctgccccccg atgcccacaa gcccctgggg gaggcagtt tccggacccc catccaagag    900
gagcaggccg acgcccactc cacccctggcc aagatcagag tgaagttcag caggagcgca    960
gacgcccccg cgtaccagca gggccagaac cagctctata cgagctcaa tctaggacga    1020 agagaggagt acgatgtttt ggacaagaga cgtggccggg accctgagat gggggaaag    1080 ccgagaagga gaaccctca ggaaggcctg tacaatgaac tgcagaaaga taagatggcg    1140
gaggcctaca gtgagattgg gatgaaaggc gagcgccgga ggggcaaggg gcacgatggc    1200
ctttaccagg gtctcagtac agccaccaag gacacctacg acgcccttca catgcaggcc    1260
ctgcctcctc gctaa                                                    1275

<210> SEQ ID NO 17
<211> LENGTH: 1197
<212> TYPE: DNA
<213> ORGANISM: Artificial Sequence
<220> FEATURE:
<223> OTHER INFORMATION: Nucleic acid sequences coding for a CAR
      (dAPRIL-HNG-CD28OXZ)

<400> SEQUENCE: 17
atggagaccg acaccctgct gctgtgggtg ctgctgctgt gggtgccagg cagcaccggc     60
agcgtgctcc acctggtgcc catcaacgcc accagcaagg acgactctga tgtgaccgag    120
gtgatgtggc agccagccct gagacggggc agaggcctgc aggcccaggg ctacggcgtg    180
agaatccagg acgctggcgt gtacctgctg tactcccagg tgctgttcca ggacgtgacc    240
ttcacaatgg gccaggtggt gagccgggag ggccagggca gacaggagac cctgttccgg    300
tgcatccgga gcatgcccag ccaccccgac agagcctaca cagctgcta cagcgctggc     360 gtgtttcacc tgcaccaggg cgacatcctg agcgtgatca tccccagagc cagagccaag    420
ctgaacctgt ccccccacgg caccttctg ggcttcgtga agctgtctgg aggcggctcg     480
gatcccgccg agcccaaatc tcctgacaaa actcacacat gcccaccgtg cccaaaagat    540
cccaaatttt gggtgctggt ggtggttggt ggagtcctgg cttgctatag cttgctagta    600
acagtggcct ttattatttt ctgggtgagg agtaagagga gcaggctcct gcacagtgac    660
tacatgaaca tgactccccg ccgcccggg cccacccgca agcattacca gccctatgcc    720
ccaccacgcg acttcgcagc ctatcgctcc aggaccaga ggctgccccc cgatgcccac    780 aagcccctg gggaggcag tttccggacc cccatccaag aggagcaggc cgacgcccac    840
tccaccctgg ccaagatcag agtgaagttc agcaggagcg cagacgcccc cgcgtaccag    900
```

| | |
|---|---|
| cagggccaga accagctcta taacgagctc aatctaggac gaagagagga gtacgatgtt | 960 |
| ttggacaaga gacgtggccg ggaccctgag atggggggaa agccgagaag gaagaaccct | 1020 |
| caggaaggcc tgtacaatga actgcagaaa gataagatgg cggaggccta cagtgagatt | 1080 |
| gggatgaaag gcgagcgccg gaggggcaag gggcacgatg gcctttacca gggtctcagt | 1140 |
| acagccacca aggacaccta cgacgccctt cacatgcagg ccctgcctcc tcgctaa | 1197 |

<210> SEQ ID NO 18
<211> LENGTH: 1902
<212> TYPE: DNA
<213> ORGANISM: Artificial Sequence
<220> FEATURE:
<223> OTHER INFORMATION: Nucleic acid sequences coding for a CAR
      (dAPRIL-HCH2CH3pvaa-CD28OXZ)

<400> SEQUENCE: 18

| | |
|---|---|
| atgggcacct ccctgctgtg ctggatggcc ctgtgcctgc tgggagccga ccacgccgac | 60 |
| ggcaagccca ttcccaaccc cctgctgggc ctggactcca cctctggcgg aggcggcagc | 120 |
| gtgctgcacc tggtgcccat caacgccacc agcaaggacg actctgatgt gaccgaggtg | 180 |
| atgtggcagc cagccctgag acggggcaga ggcctgcagg cccagggcta cggcgtgaga | 240 |
| atccaggacg ctggcgtgta cctgctgtac tcccaggtgc tgttccagga cgtgaccttc | 300 |
| acaatgggcc aggtggtgag ccgggagggc caggggcagac aggagaccct gttccgtgc | 360 |
| atccggagca tgcccagcca ccccgacaga gcctacaaca gctgctacag cgctggcgtg | 420 |
| tttcacctgc accagggcga catcctgagc gtgatcatcc cagagccag agccaagctg | 480 |
| aacctgtccc ccacggcac ctttctgggc ttcgtgaagc tgtctggagg cggctcggat | 540 |
| cccgccgagc ccaaatctcc tgacaaaact cacacatgcc caccgtgccc agcacctccc | 600 |
| gtggccggcc cgtcagtctt cctcttcccc ccaaaaccca aggacaccct catgatcgcc | 660 |
| cggacccctg aggtcacatg cgtggtggtg gacgtgagcc acgaagaccc tgaggtcaag | 720 |
| ttcaactggt acgtggacgg cgtggaggtg cataatgcca agacaaagcc gcgggaggag | 780 |
| cagtacaaca gcacgtaccg tgtggtcagc gtcctcaccg tcctgcacca ggactggctg | 840 |
| aatggcaagg agtacaagtg caaggtctcc aacaaagccc tcccagcccc catcgagaaa | 900 |
| accatctcca aagccaaagg gcagccccga gaaccacagg tgtacaccct gcccccatcc | 960 |
| cgggatgagc tgaccaagaa ccaggtcagc ctgacctgcc tggtcaaagg cttctatccc | 1020 |
| agcgacatcg ccgtggagtg ggagagcaat gggcaaccgg agaacaacta caagaccacg | 1080 |
| cctcccgtgc tggactccga cggctccttc ttcctctaca gcaagctcac cgtggacaag | 1140 |
| agcaggtggc agcaggggaa cgtcttctca tgctccgtga tgcatgaggc tctgcacaac | 1200 |
| cactacacg agaagagcct ctccctgtct ccgggtaaaa aagatcccaa atttggttgtg | 1260 |
| ctggtggtgg ttggtggagt cctggcttgc tatagcttgc tagtaacagt ggcctttatt | 1320 |
| attttctggg tgaggagtaa gaggagcagg ctcctgcaca gtgactacat gaacatgact | 1380 |
| ccccgccgcc ccgggcccac ccgcaagcat taccagccct atgccccacc acgcgacttc | 1440 |
| gcagcctatc gctccaggga ccagaggctg cccccgatg cccacaagcc cctgggggga | 1500 |
| ggcagtttcc ggacccccat ccaagaggag caggccgacg cccactccac cctggccaag | 1560 |
| atcagagtga agttcagcag gagcgcagac gcccccgcgt accagcaggg ccagaaccag | 1620 |
| ctctataacg agctcaatct aggacgaaga gaggagtacg atgtttttgga caagagacgt | 1680 |
| ggccgggacc ctgagatggg gggaaagccg agaaggaaga accctcagga aggcctgtac | 1740 |

```
aatgaactgc agaaagataa gatggcggag gcctacagtg agattgggat gaaaggcgag      1800
cgccggaggg gcaaggggca cgatggcctt taccagggtc tcagtacagc caccaaggac      1860
acctacgacg cccttcacat gcaggccctg cctcctcgct aa                        1902
```

<210> SEQ ID NO 19
<211> LENGTH: 1332
<212> TYPE: DNA
<213> ORGANISM: Artificial Sequence
<220> FEATURE:
<223> OTHER INFORMATION: Nucleic acid sequences coding for a CAR
      (dAPRIL-CD8STK-CD28OXZ)

<400> SEQUENCE: 19

```
atgggcacct ccctgctgtg ctggatggcc ctgtgcctgc tgggagccga ccacgccgac        60
ggcaagccca ttcccaaccc cctgctgggc ctggactcca cctctggcgg aggcggcagc       120
gtgctgcacc tggtgcccat caacgccacc agcaaggacg actctgatgt gaccgaggtg       180
atgtggcagc cagccctgag acggggcaga ggcctgcagg cccagggcta cggcgtgaga       240
atccaggacg ctggcgtgta cctgctgtac tcccaggtgc tgttccagga cgtgaccttc       300
acaatgggcc aggtggtgag ccgggagggc caggggcagac aggagaccct gttccggtgc       360
atccggagca tgcccagcca ccccgacaga gcctacaaca gctgctacag cgctggcgtg       420
tttcacctgc accagggcga catcctgagc gtgatcatcc cagagccag agccaagctg       480 aacctgtccc ccacggcac cttcctgggc ttcgtgaagc tgtctggagg cggctcggat       540
cccaccacga cgccagcgcc gcgaccacca caccggcgc ccaccatcgc gtcgcagccc       600
ctgtccctgc gcccagaggc gtgccggcca cggcggggg gcgcagtgca cacgaggggg       660
ctggacttcg cctgtgatat cttttggggtg ctggtggtgg ttggtggagt cctggcttgc       720
tatagcttgc tagtaacagt ggcctttatt attttctggg tgaggagtaa gaggagcagg       780
ctcctgcaca gtgactacat gaacatgact ccccgccgcc ccgggcccac ccgcaagcat       840
taccagccct atgcccacc acgcgacttc gcagcctatc gctccaggga ccagaggctg       900 cccccgatg cccacaagcc cctggggga ggcagtttcc ggaccccat ccaagaggag       960 caggccgacg cccactccac cctggccaag atcagagtga agttcagcag gagcgcagac      1020
gcccccgcgt accagcaggg ccagaaccag ctctataacg agctcaatct aggacgaaga      1080
gaggagtacg atgttttgga caagagacgt ggccgggacc ctgagatggg gggaaagccg      1140
agaaggaaga accctcagga aggcctgtac aatgaactgc agaaagataa gatggcggag      1200
gcctacagtg agattgggat gaaaggcgag cgccggaggg gcaaggggca cgatggcctt      1260
taccagggtc tcagtacagc caccaaggac acctacgacg cccttcacat gcaggccctg      1320
cctcctcgct aa                                                          1332
```

<210> SEQ ID NO 20
<211> LENGTH: 1254
<212> TYPE: DNA
<213> ORGANISM: Artificial Sequence
<220> FEATURE:
<223> OTHER INFORMATION: Nucleic acid sequences coding for a CAR
      (dAPRIL-HNG-CD28OXZ)

<400> SEQUENCE: 20

```
atgggcacct ccctgctgtg ctggatggcc ctgtgcctgc tgggagccga ccacgccgac        60
ggcaagccca ttcccaaccc cctgctgggc ctggactcca cctctggcgg aggcggcagc       120
gtgctgcacc tggtgcccat caacgccacc agcaaggacg actctgatgt gaccgaggtg       180
```

```
atgtggcagc cagccctgag acggggcaga ggcctgcagg cccagggcta cggcgtgaga    240
atccaggacg ctggcgtgta cctgctgtac tcccaggtgc tgttccagga cgtgaccttc    300
acaatgggcc aggtggtgag ccgggagggc cagggcagac aggagaccct gttccggtgc    360
atccggagca tgcccagcca ccccgacaga gcctacaaca gctgctacag cgctggcgtg    420
tttcacctgc accagggcga catcctgagc gtgatcatcc cagagccag agccaagctg     480 aacctgtccc cccacggcac ctttctgggc ttcgtgaagc tgtctggagg cggctcggat    540
cccgccgagc ccaaatctcc tgacaaaact cacacatgcc caccgtgccc aaaagatccc    600
aaattttggg tgctggtggt ggttggtgga gtcctggctt gctatagctt gctagtaaca    660
gtggccttta ttattttctg ggtgaggagt aagaggagca ggctcctgca cagtgactac    720
atgaacatga ctccccgccg ccccgggccc accgcaagc attaccagcc ctatgcccca    780
ccacgcgact tcgcagccta tcgctccagg gaccagaggc tgcccccga tgcccacaag    840 cccctgggg gaggcagttt ccggaccccc atccaagagg agcaggccga cgcccactcc     900
accctggcca agatcagagt gaagttcagc aggagcgcag acgccccgc gtaccagcag     960 ggccagaacc agctctataa cgagctcaat ctaggacgaa gagaggagta cgatgttttg    1020
gacaagagac gtggccggga ccctgagatg gggggaaagc cgagaaggaa gaaccctcag    1080
gaaggcctgt acaatgaact gcagaaagat aagatggcgg aggcctacag tgagattggg    1140
atgaaaggcg agcgccggag gggcaagggg cacgatggcc tttaccaggg tctcagtaca    1200
gccaccaagg acacctacga cgcccttcac atgcaggccc tgcctcctcg ctaa          1254
```

<210> SEQ ID NO 21
<211> LENGTH: 6
<212> TYPE: PRT
<213> ORGANISM: Artificial Sequence
<220> FEATURE:
<223> OTHER INFORMATION: Furin cleavage site

<400> SEQUENCE: 21

```
Lys Gln Lys Lys Gln Lys
1               5
```